United States Patent
Marine

(10) Patent No.: US 9,408,885 B2
(45) Date of Patent: Aug. 9, 2016

(54) COMBINATIONS OF THERAPEUTIC AGENTS FOR TREATING MELANOMA

(71) Applicants: VIB VZW, Ghent (BE);
KATHOLIEKE UNIVERSITEIT LEUVEN, K.U. LEUVEN R&D, Leuven (BE)

(72) Inventor: Jean-Christophe Marine, Erbisoeul (BE)

(73) Assignees: VIB VZW, Ghent (BE);
KATHOLIEKE UNIVERSITEIT LEUVEN, K.U. LEUVEN R&D, Leuven (BE)

(*) Notice: Subject to any disclaimer, the term of this patent is extended or adjusted under 35 U.S.C. 154(b) by 32 days.

(21) Appl. No.: 13/689,380

(22) Filed: Nov. 29, 2012

(65) Prior Publication Data
US 2013/0330421 A1 Dec. 12, 2013

Related U.S. Application Data

(60) Provisional application No. 61/565,852, filed on Dec. 1, 2011.

(51) Int. Cl.
| | |
|---|---|
| C07K 7/00 | (2006.01) |
| A61K 38/02 | (2006.01) |
| A61K 33/24 | (2006.01) |
| A61K 31/496 | (2006.01) |
| A61K 31/195 | (2006.01) |
| C12Q 1/68 | (2006.01) |
| G01N 33/50 | (2006.01) |
| G01N 33/574 | (2006.01) |
| A61K 45/06 | (2006.01) |
| A61K 38/18 | (2006.01) |
| A61K 38/30 | (2006.01) |

(52) U.S. Cl.
CPC ............. *A61K 38/02* (2013.01); *A61K 31/195* (2013.01); *A61K 31/496* (2013.01); *A61K 33/24* (2013.01); *A61K 38/1866* (2013.01); *A61K 38/30* (2013.01); *A61K 45/06* (2013.01); *C12Q 1/6886* (2013.01); *G01N 33/5005* (2013.01); *G01N 33/5743* (2013.01); *C12Q 2600/156* (2013.01); *G01N 2800/52* (2013.01)

(58) Field of Classification Search
CPC ........................................................ C07K 7/00
USPC ........................................................ 514/19.3
See application file for complete search history.

(56) References Cited

U.S. PATENT DOCUMENTS

| | | | |
|---|---|---|---|
| 5,747,498 A | 5/1998 | Schnur et al. | |
| 2012/0129871 A1* | 5/2012 | Berghausen et al. | 514/253.05 |

FOREIGN PATENT DOCUMENTS

| | | |
|---|---|---|
| EP | 566226 A1 | 11/1995 |
| EP | 520722 A1 | 12/1996 |
| EP | 787722 A1 | 8/1997 |
| EP | 837063 A1 | 4/1998 |
| EP | 564409 A1 | 1/2000 |
| WO | 9503283 | 2/1995 |
| WO | 9630347 | 10/1996 |
| WO | 9633980 | 10/1996 |
| WO | 9702266 | 1/1997 |
| WO | 9730034 | 9/1997 |
| WO | 9738983 | 10/1997 |
| WO | 9749688 | 12/1997 |
| WO | WO 9801467 | * 1/1998 |
| WO | 9810767 | 3/1998 |
| WO | 9903854 | 1/1999 |
| WO | 0009495 A1 | 2/2000 |
| WO | 0222577 A2 | 3/2002 |
| WO | 02083138 A1 | 10/2002 |
| WO | 02083139 A1 | 10/2002 |
| WO | 02083140 A1 | 10/2002 |
| WO | 02083675 A2 | 10/2002 |
| WO | 03086279 A2 | 10/2003 |
| WO | 03086394 A1 | 10/2003 |
| WO | 03086403 A1 | 10/2003 |
| WO | 03086404 A1 | 10/2003 |

(Continued)

OTHER PUBLICATIONS

Hersey et al. (Annals of Oncology, 2009, 20 (Supplement 6): vi35-vi40).*

(Continued)

*Primary Examiner* — Yan Xiao
(74) *Attorney, Agent, or Firm* — TraskBritt P.C.

(57) ABSTRACT

The present disclosure relates to the field of oncology, more particularly to the field of melanoma. Provided are methods of treating melanoma, particularly advanced cutaneous melanoma, with a combination of pharmaceutical agents comprising MDM4-specific antagonists (such as an inhibitor of the MDM4-p53 interaction or a molecule that decreases MDM4 protein stability) or MDM4-MDM2 dual inhibitors (i.e., molecules that disrupt the interactions between p53 and MDM2 and p53 and MDM4) and one or more chemotherapeutic agents such as for example alkylating agents (i.e., Dacarbazine (DITC) or melphalan), alkylating-like agents (i.e., cisplatin or carboplatin) or mitotic inhibitors (taxanes docetaxel or paclitaxel) and PI3K-AKT, B-RAF and MEK inhibitors. Further provided are pharmaceutical formulations of MDM4-specific antagonists (be it an inhibitor of the MDM4-p53 interaction or a molecule that decreases MDM4 protein stability) or MDM4-MDM2 dual inhibitors (i.e., molecules that disrupt the interactions between p53 and MDM2 and p53 and MDM4) and a pharmaceutical formulation of one or more chemotherapeutic agents such as for example alkylating agents (i.e., Dacarbazine (DITC) or melphalan), alkylating-like agents (i.e., cisplatin or carboplatin) or mitotic inhibitors (taxanes docetaxel or paclitaxel) and B-RAF and MEK inhibitors.

12 Claims, 10 Drawing Sheets

(56) References Cited

FOREIGN PATENT DOCUMENTS

| | | |
|---|---|---|
| WO | 2004041162 A2 | 5/2004 |
| WO | 2004096129 A2 | 11/2004 |
| WO | 2004096130 A2 | 11/2004 |
| WO | 2004096131 A2 | 11/2004 |
| WO | 2004096135 A2 | 11/2004 |
| WO | 2005032548 A1 | 4/2005 |
| WO | 2005037273 A1 | 4/2005 |
| WO | 2005037285 A1 | 4/2005 |
| WO | 2005049603 A1 | 6/2005 |
| WO | 2005075425 A2 | 8/2005 |
| WO | 2005100344 A1 | 10/2005 |
| WO | 2005100356 A1 | 10/2005 |
| WO | 2005112932 A2 | 12/2005 |
| WO | 2006036395 A2 | 4/2006 |
| WO | 2006040569 A1 | 4/2006 |
| WO | 2006050800 A1 | 5/2006 |
| WO | 2006065601 A2 | 6/2006 |
| WO | 2006068796 A2 | 6/2006 |
| WO | 2006076706 A1 | 7/2006 |
| WO | 2006084015 A2 | 8/2006 |
| WO | 2006091395 A2 | 8/2006 |
| WO | 2006102079 A1 | 9/2006 |
| WO | 2006105844 A1 | 10/2006 |
| WO | 2006108482 A1 | 10/2006 |
| WO | 2006110638 A2 | 10/2006 |
| WO | 2006124780 A2 | 11/2006 |
| WO | 2006124874 A2 | 11/2006 |
| WO | 2006125101 A2 | 11/2006 |
| WO | 2006135627 A2 | 12/2006 |
| WO | 2007027855 A2 | 3/2007 |
| WO | 2007031428 A1 | 3/2007 |
| WO | 2007056625 A2 | 5/2007 |
| WO | 2007067444 A1 | 6/2007 |
| WO | 2007076092 A2 | 7/2007 |
| WO | 2007090141 A2 | 8/2007 |
| WO | 2007115670 A1 | 10/2007 |
| WO | 2007123892 A2 | 11/2007 |
| WO | 2008028141 A2 | 3/2008 |
| WO | 2008030448 A1 | 3/2008 |
| WO | 2008034008 A2 | 3/2008 |
| WO | 2008055842 A1 | 5/2008 |
| WO | 2008070016 A2 | 6/2008 |
| WO | 2008070041 A2 | 6/2008 |
| WO | 2008070134 A1 | 6/2008 |
| WO | 2008079277 A1 | 7/2008 |
| WO | 2008095063 A1 | 8/2008 |
| WO | 2008016507 A2 | 9/2008 |
| WO | 2008115263 A2 | 9/2008 |
| WO | 2008119741 A2 | 10/2008 |
| WO | 2008130614 A2 | 10/2008 |
| WO | 2008140850 A1 | 11/2008 |
| WO | 2009006389 A2 | 1/2009 |
| WO | 2009006404 A2 | 1/2009 |
| WO | 2009021869 A1 | 2/2009 |
| WO | 2009039387 A1 | 3/2009 |
| WO | 2009059272 A1 | 5/2009 |
| WO | 2009100536 A1 | 8/2009 |
| WO | 2009108827 A1 | 9/2009 |
| WO | 2009108838 A1 | 9/2009 |
| WO | 2009111260 A1 | 9/2009 |
| WO | 2009115572 A2 | 9/2009 |
| WO | 2009148887 A1 | 12/2009 |
| WO | 2009148916 A1 | 12/2009 |
| WO | 2009149339 A2 | 12/2009 |
| WO | 2010032986 A2 | 3/2010 |
| WO | 2010065893 A1 | 6/2010 |
| WO | 2010078408 A1 | 7/2010 |
| WO | 2010100127 A1 | 9/2010 |
| WO | 2010104933 A1 | 9/2010 |
| WO | 2010104973 A1 | 9/2010 |
| WO | 2010111527 A1 | 9/2010 |
| WO | 2011005219 A1 | 1/2011 |
| WO | 2011023677 A1 | 3/2011 |
| WO | 2011023773 A1 | 3/2011 |
| WO | 2011025927 A1 | 3/2011 |
| WO | 2011025968 A1 | 3/2011 |
| WO | 2011028540 A1 | 3/2011 |
| WO | 2011076786 A1 | 6/2011 |
| WO | 2011085269 A1 | 7/2011 |
| WO | 2011090738 A1 | 7/2011 |
| WO | 2011097526 A1 | 8/2011 |
| WO | 2011097594 A1 | 8/2011 |
| WO | 2011117381 A1 | 9/2011 |
| WO | 2011119894 A2 | 9/2011 |

OTHER PUBLICATIONS

Wiesenthal, (Human Tumor Assay Journal, on-line at http://weisenthal.org/synergy1.htm, Mar. 14, 2012).*
Berenbaum (Clin exp Immunol, 1997, 28:1-18).*

* cited by examiner

COMBINATIONS OF THERAPEUTIC AGENTS FOR TREATING MELANOMA

CROSS-REFERENCE TO RELATED APPLICATION

This application claims the benefit of U.S. Provisional Patent Application Ser. No. 61/565,852, filed Dec. 1, 2011, the disclosure of which is hereby incorporated herein in its entirety by this reference.

TECHNICAL FIELD

Demonstrated herein, MDM4, a negative regulator of p53, is up-regulated in ~60% of human cutaneous melanomas. Accordingly, treatment of metastatic melanoma cells with a specific inhibitor of the MDM4-p53 interaction decreases cell viability irrespective of their sensitivity to B-RAF-inhibitors and greatly synergizes with BRAF inhibitors in cell killing. In addition, MDM4 targeting also greatly sensitizes metastatic melanoma cells to conventional chemotherapeutics.

BACKGROUND

Cutaneous malignant melanoma is the leading cause of skin cancer-related deaths. Its incidence has increased worldwide faster than any other cancer, with 5-year survival rates for patients with distant metastatic disease being less than 20% (see the world wide web at seer.cancer.gov/csr/1975_2007). Improvement of clinical outcomes for this aggressive, chemo- and radio-resistant, disease remains a major clinical challenge. Significant progress in our understanding of the etiologies and genetic underpinnings of melanoma has nevertheless been made.[1, 2] These advances have recently led to promising results in trials of targeted therapies for this disease.[3] The Ras/Raf/MEK/ERK pathway has been identified as the main regulator of cell proliferation in melanoma, with ERK being hyperactivated in up to 90% of human melanomas.[4] Activating NRAS mutations are a common route to activating this pathway; mutations affecting codon 61 being the most prevalent (NRAS$^{Q61K}$).[5, 6]

BRAF, one of the three human RAF genes, is also frequently mutated in melanomas,[7] with the most common mutation being a glutamic acid for valine substitution at position 600 (V600E).[7] BRAF$^{V600E}$ stimulates constitutive ERK signaling, leading to melanocyte hyper-proliferation.[8] Early clinical experience with the novel class I RAF-selective inhibitor, PLX4032, demonstrated an unprecedented 80% anti-tumor response rate among patients with BRAF$^{V600E}$-positive melanomas; unfortunately, patients acquire drug resistance within a few months of an initial response.[9] Because of its ability to acquire drug resistance, its chemoresistance and because melanoma is a highly dynamic and genetically heterogeneous tumor, novel treatment strategies and combination therapies are urgently needed. Restoration of the wild-type p53 tumor suppressor function has emerged as an attractive anti-cancer strategy for many tumor types.[10-12]

Whether this approach can be therapeutically beneficial in malignant melanoma remains unknown. p53 pathway inactivation, which mainly arises as a consequence of inactivating mutations or allelic loss of the p53 gene itself, is the most common molecular defect in human cancers.[13] Intriguingly, the p53 locus is intact in over 95% of melanoma cases,[14] raising questions as to the pathogenic relevance of p53 in the etiology of melanoma tumor formation. At the same time, there is an increasing body of evidence supporting a relevant role for p53 in melanoma development. Loss of p53 cooperates with melanocyte-specific overexpression of activated HRAS$^{V12G}$ and BRAF$^{V600E}$ in promoting melanomagenesis in mice[15, 16] and oncogenic NRAS cooperates with p53 loss to generate melanomas in zebrafish.[17]

Cancers that retain expression of wild-type p53 often find alternative ways to subvert p53 function, through either deregulation of upstream modulators and/or inactivation of downstream effectors.[18] MDM2, which encodes an E3 ubiquitin ligase that control p53 levels and function,[19] is amplified in human melanomas but only in 3%-5% of documented cases.[20] The INK4A-ARF (CDKN2A) locus is often deleted or inactivated in heritable and sporadic melanoma.[1] This locus encodes two distinct tumor suppressors, p16$^{INK4A}$ (referred hereafter as INK4A) and p14$^{ARF}$ (referred hereafter as ARF). INK4A positively regulates the pRB tumor suppressor and ARF is a potent MDM2 antagonist. Thus, decreased ARF expression or its complete loss could, in part, compromise p53 function in melanoma.[21] However, p53-independent functions of ARF have been described[22] and whether ARF restricts melanoma progression in a p53-dependent manner is still a matter of debate.[23] Overall, although several oncogenic events that compromise p53 function have been described in melanoma the number and the frequency of these events accounts for only a small proportion of melanoma cases, implying that additional, unidentified, mechanisms exist. Unveiling such mechanisms may lead to the development of novel targeted therapeutic strategies allowing re-activation of p53 tumor killing activities.

DISCLOSURE

Described herein is evidence that the p53 pathway is inactivated in the majority of cutaneous melanomas as a result of deregulated expression of MDM4 (also known as HDMX or MDMX), a key negative regulator of p53[24, 25] Further demonstrated is that targeting the MDM4-p53 interaction inhibits the growth of melanoma cells in vitro and in vivo and significantly sensitizes them to conventional chemotherapeutics. Also surprisingly, we show that MDM4 knockdown and the use of inhibitors of the p53-MDM2 interaction affect the growth of melanoma cells that have acquired resistance to BRAF inhibitors and also synergize with BRAF inhibitors in killing BRAF-mutant cells. Together, our results identify the MDM4-p53 interaction as a key therapeutic target for melanoma treatment and a promising new candidate for combined therapy for this aggressive tumor type. Accordingly, it has been surprisingly found that MDM4-inhibitors are synergistic (act synergistically) when used in combination with chemotherapeutic agents. Importantly, compelling evidence—including mouse genetic experiments—indicates that MDM4 targeting will not affect the viability of normal (non-cancer) cells. Therapeutic effects of combinations of chemotherapeutic agents with an MDM4-inhibitor is therefore expected to result in lower toxicity of the chemotherapeutic agents as their efficacy is greatly enhanced at lower doses when used in combination with MDM4 inhibitors.

In a first aspect, described herein is a method for preventing the progression or treatment of patients with malignant melanoma, which comprises administering pharmaceutically effective amounts of a combination of i) an MDM4-inhibitor and ii) one or more chemotherapeutic agents selected from a microtubule active agent, an alkylating agent, an anti-neoplastic anti-metabolite, a platin compound, a Raf kinase inhibitor and MEK kinase inhibitor, a PI3/AKT inhibitor, a topoisomerase I inhibitor, a topoisomerase II inhibitor, a VEGF inhibitor, a tyrosine kinase inhibitor, an EGFR kinase inhibitor, an mTOR kinase inhibitor, an insulin-like growth factor I inhibitor, a HDAC inhibitor, a proteasome inhibitor, and ionizing radiation for simultaneous, concurrent, separate or sequential use in for preventing or treating melanoma.

In another aspect, described herein is a method for preventing or treating of melanoma according to claim 1 wherein one or more chemotherapeutic agents are selected from camptothecin derivatives, paclitaxel, docetaxel, epothilone B, 5-FU, gemcitabine, oxaliplatin, cisplatinum, carboplatin, melphalan, dacarbazine, temozolomide, doxorubicin, imatinib, erlotinib, bevacizumab, cetuximab and PI3/AKT kinase inhibitors, Raf or MEK kinase inhibitors. In a particular aspect melanoma is cutaneous melanoma. In another particular aspect, melanoma is metastatic melanoma. In another particular aspect, melanoma has a B-RAF activating mutation. In yet another particular aspect, melanoma comprises a B-Raf activating mutation but has acquired resistance to a B-Raf kinase inhibitor. In yet another embodiment, a melanoma has a B-Raf activating mutation and has an enhanced protein expression of MDM4. In another aspect, a Raf kinase inhibitor is a B-Raf kinase inhibitor.

In another aspect, described herein is a pharmaceutical composition comprising i) an MDM4-inhibitor and ii) one or more chemotherapeutic agents selected from a microtubule active agent, an alkylating agent, an anti-neoplastic anti-metabolite, a platin compound, a Raf kinase inhibitor, a PI3/AKT kinase inhibitor, a topoisomerase I inhibitor, a topoisomerase II inhibitor, a VEGF inhibitor, a tyrosine kinase inhibitor, an EGFR kinase inhibitor, an mTOR kinase inhibitor, an insulin-like growth factor I inhibitor, a HDAC inhibitor, a proteasome inhibitor.

In yet another aspect, described herein is a pharmaceutical composition comprising as one or more chemotherapeutic agents selected from camptothecin derivatives, paclitaxel, docetaxel, epothilone B, 5-FU, gemcitabine, oxaliplatin, cisplatinum, carboplatin, melphalam, dacarbazine, temozolomide, doxorubicin, imatinib, erlotinib, bevacizumab, cetuximab and a Raf kinase inhibitor.

In yet another aspect, described herein is a pharmaceutical composition comprising as one or more chemotherapeutic agents selected from oxaliplatin, cisplatinum, carboplatin, melphalam, dacarbazine, temozolomide and a RAF kinase inhibitor.

In yet another aspect, described herein is a pharmaceutical composition comprising an MDM4 inhibitor and a B-RAF kinase inhibitor. It is submitted that, as used herein, the annotation "B-RAF" is equivalent with the annotation "BRAF."

In another aspect, described herein is a method for preventing or treating of melanoma, which comprises administering pharmaceutically effective amounts of an MDM4-inhibitor for use in for preventing or treating melanoma. In specific aspects melanoma is advanced cutaneous melanoma, or metastatic melanoma, or the melanoma has a B-Raf activating mutation, or the melanoma has a B-Raf activating mutation and has acquired resistance to B-RAF inhibitors.

In another aspect, described herein is a method for testing the eligibility of a patient suffering from melanoma for treatment with an MDM4 inhibitor comprising determining the protein expression levels of MDM4 and MDM2 in a tumor sample derived from the patient and wherein an enhanced MDM4 protein expression (as compared to the MDM2 protein expression) selects the patient as eligible for treatment.

In another aspect, described herein is a method for testing the eligibility of a patient suffering from melanoma for treatment with a pharmaceutical composition described herein before comprising determining the protein expression level of MDM4 and MDM2 and the B-RAF status in a tumor sample derived from the patient and wherein an enhanced MDM4 protein expression (as compared to the MDM2 protein expression) and the presence of a B-RAF activating mutation selects the patient as eligible for treatment.

In yet another aspect, described herein is a method for treating a patient having melanoma comprising determining the protein expression level of MDM4 in a melanoma tumor sample derived from the patient and wherein an enhanced MDM4 protein expression compared to the MDM2 protein expression selects the patient for administering a therapeutically effective amount of a pharmaceutical composition described herein before.

In yet another aspect, described herein is a method for treating a patient having melanoma comprising determining the protein expression level of MDM4 and the B-RAF status in a melanoma tumor sample derived from the patient and wherein an enhanced MDM4 protein expression compared to the MDM2 protein expression and the presence of a B-RAF mutation selects the patient for administering a therapeutically effective amount of a pharmaceutical composition described herein before.

DETAILED DESCRIPTION OF THE INVENTION

Figure 1:
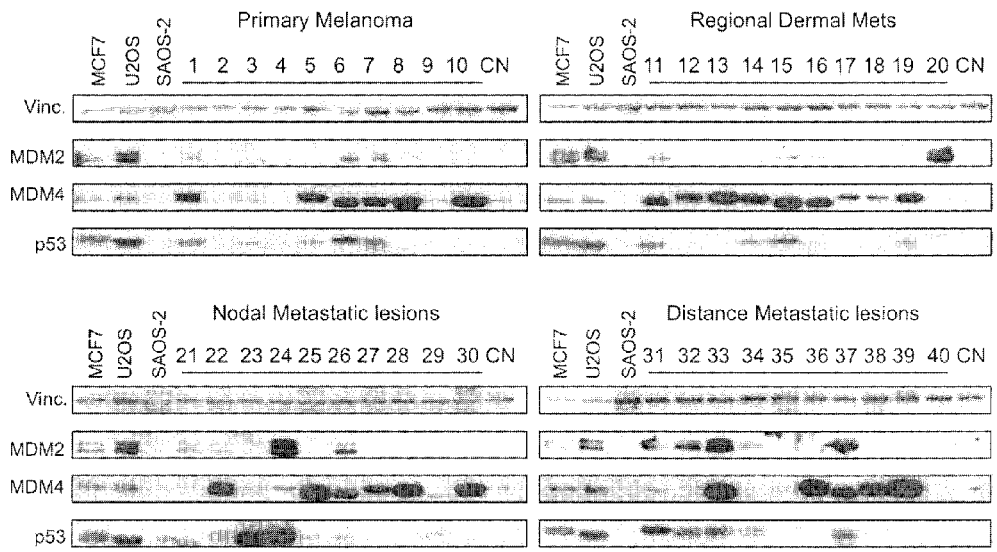
FIG. 1: MDM4 is frequently over expressed in human melanoma. Protein levels were assessed by Western blotting analysis in total lysates from human melanoma samples and cell lines. (A) Protein expression of MDM4, MDM2 and p53 in melanoma samples from human patients. The samples are divided into four categories each containing ten samples (primary, non-invasive lesions, regional dermal metastases, nodal metastatic lesions and distant metastatic lesions). Expression was evaluated in congenital melanocytic nevi (CN). (B) Expression levels of MDM4, MDM2, p53 and p21 were also determined in patient-derived short-term melanoma cell lines, in normal melanocytes (n. melan) and (C) in long-term culture human melanoma cell lines. MCF7, U2OS, SAOS-2 were used as reference controls; Vinculin (Vinc.) and Tubulin as loading controls.
Figure 1:
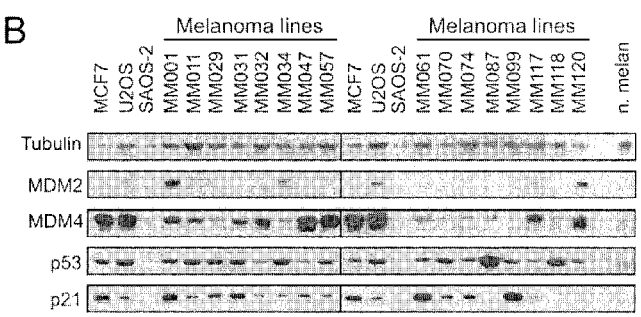
Figure 1:
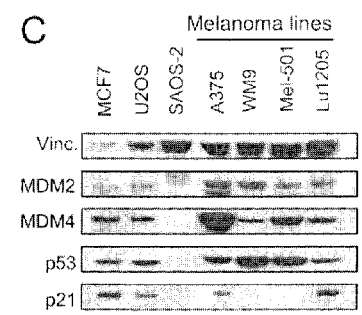

In most tumor types, p53 is silenced mainly by missense mutations or deletions of the p53 gene itself. In melanoma, however, such genomic events are rare, making the relevance of the p53 pathway in melanomagenesis irrelevant. Provided herein is evidence that increased MDM4 protein expression contributes to p53 inactivation during melanomagenesis. Indeed, we demonstrate that the MDM4 protein is over expressed in about 60% of cutaneous melanoma cases. In addition to being very frequent, MDM4 up-regulation appears to be an early oncogenic event as high MDM4 levels are observed as early as in primary, non-invasive, melanoma lesions. Notably, MDM4 overexpression is only detected at the protein level explaining why this event has been missed by transcriptomic analyses previously performed on melanoma samples. We show that most metastatic melanoma cells depend on high MDM4 protein expression to keep p53 pro-apoptotic activities in check and to survive.

Restoration of p53 function has been extensively pursued as a novel therapeutic approach to treat cancers that, like most melanomas, retain wild-type p53. Indeed, the therapeutic benefits of such an approach have been demonstrated in several preclinical mouse cancer models.[45-47] Numerous efforts have focused on blocking MDM2 as a strategy for reactivating p53 in tumors.[31, 48-51] However, several caveats to this approach have recently been uncovered.[52] One major limitation of anti-MDM2-based therapy is that tumor cells that over express MDM4 and low levels of MDM2, only poorly respond to MDM2 inhibition.[12, 40] Here, we show that most human melanoma cell lines express high MDM4 and low MDM2 levels and that representative cell lines with such MDM4/MDM2 ratio respond very poorly to nutlin-3 alone.

It was surprisingly found that human melanoma cell lines are extremely sensitive to MDM4 inhibitors. Of note, melanomas that express high levels of both MDM4 and MDM2 were found to be extremely rare. Taken together our data show that while the majority of melanoma patients would respond poorly to MDM2 inhibition they would greatly benefit from pharmacological disruption of the MDM4-p53 interaction. The prognosis of patients with metastatic melanoma (MM) remains very poor, largely reflecting the failure of conventional chemotherapy regimens to impact on advanced disease.[53] Strategies that increase the sensitivity of melanoma cells to chemotherapeutics are therefore expected to decrease their toxicity and eventually improve their potency.

It is demonstrated in the examples that a stapled peptide inhibiting the MDM4/p53 interaction (designated further in the examples as SAH-p53-8) greatly potentiates the cytotoxic effects of two chemotherapeutic agents currently used in the clinic. MDM4 inhibitors can therefore be used to enhance the effectiveness of conventional therapeutic agents in the treatment of melanoma, such as cutaneous melanoma, such as metastatic melanoma.

Yet another aspect is that the identification of activating mutations in BRAF, in 50-70% of malignant melanoma biopsies, raises the hope for targeted therapy as an attractive alternative to conventional chemotherapy in melanoma treatment. Indeed, encouraging results from a clinical trial with a small molecule BRAF inhibitor were recently reported.[54] However, chronic treatment with BRAF inhibitors was shown to be invariably associated with the development of drug resistance.[42] Strategies for overcoming intrinsic and acquired drug resistance to small molecule BRAF inhibitors are thus urgently needed.

As demonstrated convincingly herein, MDM4 overexpression occurs equally frequently in tumors harboring mutations in BRAF and NRAS, and that MDM4 inhibition equally affects the growth of both NRAS and BRAF melanoma cells. Importantly, we also show here that MDM4 inhibition is equally effective at inhibiting growth of BRAF-mutant cells that have acquired resistance to BRAF inhibitors. It is further also shown that combined treatment with MDM4 and BRAF inhibitors synergize in the killing of melanoma cells that are sensitive to the BRAF inhibitors. Thus, MDM4 targeting also offers a therapeutic avenue in cases where BRAF inhibitors are no longer effective (i.e., melanoma cells having B-RAF activating mutations that have become resistant to B-RAF inhibitors) and even against tumors harboring NRAS mutations against which no specific inhibitors exist.

Thus, in a first embodiment, provided is a method for preventing or treating of melanoma, which comprises administering pharmaceutically effective amounts of an MDM4-inhibitor for use in for preventing or treating melanoma.

In yet another embodiment, melanoma is advanced cutaneous melanoma. In yet another embodiment, melanoma is metastatic melanoma. In yet another embodiment, melanoma is a dysplastic melanocytic nevus.

In yet another embodiment, melanoma has a mutation that activates the activity of B-RAF.

In yet another embodiment, the melanoma, or subcutaneous melanoma, with an activating B-RAF mutation has acquired resistance to a B-RAF inhibitor.

In a specific embodiment, the MDM4-inhibitor is a stapled peptide such as disclosed in WO2008095063.

In yet another embodiment, provided is a method for preventing or treating of melanoma, which comprises administering pharmaceutically effective amounts of a combination of i) an MDM4-inhibitor and ii) one or more chemotherapeutic agents selected from a microtubule active agent, an alkylating agent, an anti-neoplastic anti-metabolite, a platin compound, a Raf or MEK kinase inhibitor, a PI3/AKT kinase inhibitor, a topoisomerase I inhibitor, a topoisomerase II inhibitor, a VEGF inhibitor, a tyrosine kinase inhibitor, an EGFR kinase inhibitor, an mTOR kinase inhibitor, an insulin-like growth factor I inhibitor, a HDAC inhibitor, a proteasome inhibitor, and ionizing radiation for simultaneous, concurrent, separate or sequential use in for preventing or treating melanoma.

In another embodiment, provided is a method for preventing or treating of melanoma, which comprises administering pharmaceutically effective amounts of a combination of i) an MDM4-inhibitor and ii) wherein one or more chemotherapeutic agents are selected from camptothecin derivatives, melphalan, temozolomide, dacarbazine, paclitaxel, docetaxel, epothilone B, 5-FU, gemcitabine, oxaliplatin, cisplatinum, carboplatin, doxorubicin, imatinib, erlotinib, bevacizumab, cetuximab and a Raf kinase inhibitor.

In yet another embodiment, a Raf kinase inhibitor is a B-RAF kinase inhibitor.

In yet another particular embodiment, an MDM4-inhibitor is a stapled peptide inhibitor such as disclosed in WO2008095063.

In yet another embodiment in the method for treating or preventing melanoma, the melanoma is an advanced cutaneous melanoma.

In yet another embodiment in the method for treating or preventing melanoma, the melanoma is a metastatic melanoma.

In yet another embodiment in the method for treating or preventing melanoma, the melanoma is a dysplastic nevus.

In yet another embodiment in the method for treating or preventing melanoma, the melanoma has a B-RAF activating mutation.

In yet another particular embodiment in the method for treating or preventing melanoma, the melanoma has a B-RAF$^{V600E}$ mutation as a B-RAF activating mutation.

A "B-RAF activating mutation" is a mutation that makes the B-RAF kinase constitutively active. An example of a B-RAF activating mutation is the B-RAF$^{V600E}$ mutation.

In yet another particular embodiment in the method for treating or preventing melanoma, the melanoma that has a B-RAF activating mutation has acquired a resistance to a B-RAF inhibitor. The latter means that the melanoma does not respond anymore (i.e., as measured by the lack of induction of apoptosis or lack of growth arrest when a B-RAF inhibitor is applied to such a B-RAF inhibitor resistant melanoma) to the B-RAF inhibitor treatment.

In yet another particular embodiment in the method for treating or preventing melanoma, the melanoma that has a B-RAF activating mutation has acquired a resistance to a B-RAF inhibitor and has additionally an enhanced protein expression ratio level between MDM4 and MDM2.

An MDM4-inhibitor, in the present context, is a molecule that inhibits (or disrupts, or antagonizes) the interaction between p53 and MDM4. In certain instances an MDM4-inhibitor inhibits the interaction between p53 and MDM4 and additionally also inhibits the interaction between p53 and MDM2. Inhibitors inhibiting MDM2/p53 and MDM4/p53 are known in the art as dual-specificity inhibitors. Since MDM4 is considered to be a negative regulator of p53, the effect of a molecule that inhibits the MDM4/p53 interaction is an activation of p53 that results in the initiation of cell death in a cell wherein enhanced MDM4 protein expression occurs. Preferred examples of small molecules that antagonize the MDM4/p53 interaction are an imidazole, a beta-lactam, a tetrahydroquinoline, a 2-aminomethyl phenol or a 1-(alkylsulfonyl)-4,5-dihydro-1H-imidazole. Variants of such molecules have been disclosed for example in WO2008119741, WO201123677, WO201176786 and WO2008130614, which specifications are hereby incorporated by reference. Next to small compounds, peptides have also been described that inhibit the interaction between MDM4 and p53 (or inhibit the interaction between MDM4/p53 and MDM2/p53). Examples of such peptides are disclosed in WO2008106507, WO2009149339 and WO2011005219, which specifications are hereby incorporated by reference. In a preferred embodiment, the MDM4/p53 inhibitor is a stapled peptide such as the peptides disclosed in WO2008095063, which specification is hereby incorporated by reference, in addition to the stapled peptide used in the examples.

The term "chemotherapeutic agents" is a broad one covering many chemotherapeutic agents having different mechanisms of action. Combinations of chemotherapeutic agents with MDM4-inhibitors result in synergistic effects and in improvements in melanoma cancer therapy. Generally, chemotherapeutic agents are classified according to the mechanism of action. Many of the available agents are anti-metabolites of development pathways of various tumors, or react with the DNA of the tumor cells.

By the term "chemotherapeutic agent" is meant chemotherapeutic agents selected from the list consisting of a topoisomerase I inhibitor or a derivative thereof, a microtubule active agent, an insulin-like growth factor I inhibitor, a protein tyrosine kinase inhibitor, a VEGF inhibitor, an mTOR kinase inhibitor, an EGFR kinase inhibitor, an alkylating agent, an anti-neoplastic anti-metabolite, a platin compound, a topoisomerase I1 inhibitor, proteasome inhibitors, HDAC inhibitors, PI3/AKT kinase inhibitors, RAF kinase inhibitors and tumor cell damaging approaches, such as ionizing radiation.

The term "microtubule active agent," as used herein, relates to microtubule stabilizing, microtubule destabilizing agents and microtublin polymerization inhibitors including, but not limited to taxanes, e.g., paclitaxel and docetaxel; vinca alkaloids, e.g., vinblastine, especially vinblastine sulfate; vincristine, especially vincristine sulfate and vinorelbine; discodermolides; colchicine and epothilones and derivatives thereof, e.g., epothilone B or a derivative thereof. Paclitaxel is marketed as taxol; docetaxel as taxotere; vinblastine sulfate as vinblastin and vincristine sulfate as farmistin.

The term "alkylating agent," as used herein, includes, but is not limited to, Dacarbazine (DTIC) cyclophosphamide, ifosfamide, melphalan or nitrosourea (BCNU or Gliadel), or temozolomide (temodar). Cyclophosphamide can be administered, e.g., in the form as it is marketed, e.g., under the trademark cyclostin; and ifosfamide as holoxan.

The term "anti-neoplastic anti-metabolite" includes, but is not limited to, 5-fluorouracil (5-FU); capecitabine; gemcitabine; DNA de-methylating agents, such as 5-azacytidine and decitabine; methotrexate; edatrexate; and folic acid antagonists. Capecitabine can be administered, e.g., in the form as it is marketed, e.g., under the trademark xeloda; and gemcitabine as gemzar.

The term "platin compound," as used herein, includes, but is not limited to, carboplatin, cisplatin, cisplatinum, oxaliplatin, satraplatin and platinum agents, such as zd0473. Carboplatin can be administered, e.g., in the form as it is marketed, e.g., carboplat; and oxaliplatin as eloxatin. Please note that in the field of oncology the platin compound are often designated as alkylating-like compounds.

The term "topoisomerase I inhibitors," as used herein, includes derivatives of the plant compound camptothecin. Irinotecan (CPT-11) is a semi-synthetic derivative of camptothecin. Topotecan is another semi-synthetic analogue of camptothecin. There are other derivatives of camptothecin, as well as new formulations of the parent plant extract, that are in various stages of clinical trials.

The term "topoisomerase I1 inhibitor," as used herein, includes, but is not limited to, the anthracyclines, such as doxorubicin, including liposomal formulation, e.g., caelyx;

daunorubicin, including liposomal formulation, e.g., daunosome; epirubicin; idarubicin and nemorubicin; the anthraquinones mitoxantrone and losoxantrone; and the podophillotoxines etoposide and teniposide. Etoposide is marketed as etopophos; teniposide as VM 26-bristo; doxorubicin as adriblastin or adriamycin; epirubicin as farmorubicin; idarubicin as zavedos; and mitoxantrone as novantron.

The term "a VEGF inhibitor" includes, but is not limited to, compounds targeting, decreasing or inhibiting the activity of the vascular endothelial growth factor (VEGF) receptors, such as compounds that target, decrease or inhibit the activity of VEGF, especially compounds that inhibit the VEGF receptor, such as, but not limited to, 7/-/-pyrrolo[2,3-d]pyrimidine derivative; BAY 43-9006; isolcholine compounds disclosed in WO 00/09495, such as (4-tert-butyl-phenyl)-94-pyridin-4-ylmethyl-isoquinolin-1-yl)-amine.

The term "insulin-like growth factor I inhibitor" relates to compounds targeting, decreasing or inhibiting the activity of the insulin-like growth factor receptor 1 (IGF-1 R), such as compounds that target, decrease or inhibit the activity of IGF-IR, especially compounds that inhibit the IGF-1 R receptor. Compounds include, but are not limited to, the compounds disclosed in WO02/092599 and derivatives thereof of 4-amino-5-phenyl-7-cyclobutyl-pyrrolo{2,3-pyrimidine derivatives. The term a "protein tyrosine kinase," as used herein, relates to compounds targeting, decreasing or inhibiting the activity of protein-tyrosine kinase, such as imatinib mesylate (gleevec), tyrphostin orpyrymidylaminobenzamide and derivatives thereof. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810, AG 99, Tyrphostin AG 213, Tyrphostin AG 1748, Tyrphostin AG 490, Tyrphostin B44, Tyrphostin B44 (+) enantiomer, Tyrphostin AG 555, AG 494, Tyrphostin AG 556; AG957; and adaphostin (4-{[(2,5-dihydroxyphenyl)methyl]amino}-benzoic acid adamantyl ester; NSC 680410, adaphostin).

The term "EGFR kinase inhibitor," as used herein, relates to compounds targeting, decreasing or inhibiting the activity of the epidermal growth factor family of receptor tyrosine kinases (EGFR, ErbB2, ErbB3, ErbB4 as homo- or heterodimers), such as compounds that target, decrease or inhibit the activity of the epidermal growth factor receptor family are especially compounds, proteins or antibodies that inhibit members of the EGF receptor tyrosine kinase family, e.g., EGF receptor, ErbB2, ErbB3 and ErbB4 or bind to EGF or EGF-related ligands, and are in particular those compounds, proteins or monoclonal antibodies generically and specifically disclosed in WO97/02266, e.g., the compound of Example 39, or in EP0564409, WO99/03854, EP0520722, EP0566226, EP0787722, EP0837063, U.S. Pat. No. 5,747, 498, WO98/10767, WO97/30034, WO97/49688, WO97/38983 and WO 96/30347, e.g., compound known as CP358774, WO96/33980, e.g., compound ZD1839; and WO95/03283, e.g., compound ZM105180, e.g., trastuzumab (HERCEPTIN), cetuximab, iressa, OSI-774, CI-1033, EKB-569, GW-2016, E1.1, E2.4, E2.5, E6.2-E6.4, E2.11, E6.3 or E7.6.3, and erlotinib and gefitinib. Erlotinib can be administered in the form as it is marketed, e.g., tarceva, and gefitinib as iressa, human monoclonal antibodies against the epidermal growth factor receptor including ABX-EGFR.

The term "mTOR kinase inhibitor" refers to compounds that target, decrease or inhibit the activity/function of serine/theronine mTOR kinase are especially compounds, proteins or antibodies that target/inhibit members of the mTOR kinase family, e.g., RAD, RAD001, CCI-779, ABT578, SAR543, rapamycin and derivatives/analogs thereof, AP23573 and AP23841 from Ariad, everolimus (certican) and sirolimus.

The term "proteasome inhibitors," as used herein, includes compounds that target, decrease or inhibit the activity of the proteosome. Compounds that target, decrease or inhibit the activity of the proteosome include, but are not limited to, PS-341; MLN 341, bortezomib or velcade. The term "HDAC inhibitor," as used herein, relates to relates to compounds that inhibit the histone deacetylase and that possess anti-proliferative activity. This includes, but is not limited to, compounds disclosed in WO 02/22577. It further especially includes suberoylanilide hydroxamic acid (SAHA); [4-(2-amino-phenylcarbamoyl)-benzyl]-carbamic acid pyridine-3-ylmethyl ester and derivatives thereof; butyric acid, pyroxamide, trichostatin A, oxamflatin, apicidin, depsipeptide, depudecin and trapoxin.

The term "tumor cell damaging approaches" refers to approaches, such as ionizing radiation.

The term "ionizing radiation," referred to above and hereinafter, means ionizing radiation that occurs as either electromagnetic rays, such as X-rays and gamma rays; or particles, such as alpha, beta and gamma particles. Ionizing radiation is provided in, but not limited to, radiation therapy and is known in the art. See Hellman, Cancer, 4$^{th}$ Edition, Vol. 1, Devita et al., Eds., pp. 248-275 (1993).

A "RAF kinase inhibitor" refers to compounds (or "inhibitors" or "antagonists," which are equivalent terms) that interfere with the abnormal activation of a RAF kinase. The meaning of "abnormal activation of a RAF kinase" is further explained. The Ras/Raf/Mek/ERK (mitogen-activated protein kinase) signaling pathway plays a critical role in transmitting proliferation signals generated by the cell surface receptors and cytoplasmic signaling elements to the nucleus. Constitutive activation of this pathway is involved in malignant transformation by several oncogenes. Activating mutations in RAS occur in approximately 15% of cancers, and recent data has shown that the RAF kinase, B-RAF, is mutated in about 7% of cancers (Wellbrock et al., Nature Rev. Mol. Cell. Biol. 2004, 5:875-885). In mammals, the RAF family of serine/threonine kinases comprises three members: A-RAF, B-RAF and C-RAF. However, activating mutations have so far been only identified in B-RAF underlining the importance of this isoform.

The most common cancer mutation in B-RAF results in a valine to glutamic acid exchange at position 600 of the protein (mutant is designated as BRAF$^{V600E}$) which dramatically enhances the activity of B-RAF. Thus, RAF inhibitors, particularly B-RAF inhibitors, interfere with cells comprising B-RAF mutations, in particular with cells having the B-RAF$^{V600E}$ mutation. A number of B-RAF inhibitors are described in the art and it is believed that these B-RAF inhibitors are suitable for use as described herein. The following references that disclose B-RAF inhibitors are herein incorporated by reference: WO2011117381, WO2011119894, WO2011097594, WO2011097526, WO2011085269, WO2011090738, WO2011025968, WO2011025927, WO2011023773, WO2011028540, WO2010111527, WO2010104973, WO2010100127, WO2010078408, WO2010065893, WO2010032986, WO2009115572, WO2009115572, WO2009108838, WO2009108827, WO2009111260, WO2009100536, WO2009059272, WO2009039387, WO2009021869, WO2009006404, WO2009006389, WO2009006389, WO2008140850, WO2008079277, WO2008055842, WO2008034008, WO2008115263, WO2008030448, WO2008028141, WO2007123892, WO2007115670, WO2007090141, WO2007076092, WO2007067444, WO2007056625, WO2007031428, WO2007027855, WO2006125101, WO2006124874, WO2006124780, WO2006124780, WO2006102079, WO2006108482, WO2006105844, WO2006084015, WO2006076706, WO2006050800, WO2006040569, WO2005112932, WO2005075425, WO2005049603, WO2005037285, WO2005037273 and WO2005032548.

The term "PI3/AKT kinase inhibitor," as used herein, refers to inhibitors of the phosphatidylinositol 3-kinase (PI3K)/Akt pathway. The latter pathway is considered as a critical survival-signaling pathway. Akt-mediated phosphorylation may alter the activity of proteins such as caspase-9, some Bcl-2 family members, and nuclear factor κB (NF-κB) and other transcription factors, which trigger or restrain apoptosis; and PI3K/Akt deregulation may contribute to tumorigenesis, metastasis, and resistance to chemotherapy. Inhibition of Akt activation and activity can be achieved by inhibiting PI3K with inhibitors such as LY294002 and wortmannin. In a particular embodiment a PI3/AKT kinase inhibitor is an AKT inhibitor. Akt, alternatively named as protein kinase B, is a serine/threonine kinase. Inhibitors of Akt that can be used as described herein are disclosed in WO2005/100344; WO2005/100356; WO2004/096135; WO2004/096129; WO2004/096130; WO2004/096131; WO2006/091395; WO2008/070134; WO2009/148916; WO2008/070016; WO2008/070041; WO2004/041162; WO2009/148887; WO2006/068796; WO2006/065601; WO2006/110638; WO2003/086394; WO2003/086403; WO2003/086404; WO2003/086279; WO2002/083139; WO2002/083675; WO2006/036395; WO2002/083138; WO2006/135627; WO2002/083140, WO2006/135627; WO2008/070041; WO2008/070016; WO2008/070134; WO2009/148887; WO2009/148916, WO2006/135627 and WO2010/104933.

It is understood in each case where citations of patent applications or scientific publications are given, in particular with regard to the respective compound claims and the final products of the working examples therein, the subject matter of the final products, the pharmaceutical preparations and the claims is hereby incorporated into the present application by reference to these publications. Comprised are likewise the corresponding stereoisomers, as well as the corresponding crystal modifications, e.g., solvates and polymorphs, which are disclosed therein. The compounds used as active ingredients in the combinations disclosed herein can be prepared and administered as described in the cited documents, respectively.

The structure of the active agents identified by code numbers, generic or trade names may be taken from the actual edition of the standard compendium "The Merck Index" or from databases, e.g., Patents International, e.g., IMS World Publications, or the publications mentioned above and below. The corresponding content thereof is hereby incorporated by reference.

It will be understood that references to the MDM4-inhibitors and the chemotherapeutic compounds are meant to also include the pharmaceutically acceptable salts of any of the active substances. If active substances comprised by the components have, e.g., at least one basic center, they can form acid addition salts. Corresponding acid addition salts can also be formed having, if desired, an additionally present basic center. Active substances having an acid group, e.g., COOH, can form salts with bases. The active substances comprised in the components or a pharmaceutically acceptable salt thereof may also be used in form of a hydrate or include other solvents used for crystallization.

Combination Treatment

A particular embodiment relates to a method for the prevention of treatment of melanoma, particularly advanced cutaneous melanoma, which comprises treating the patient concurrently or sequentially with pharmaceutically effective amounts of a combination of: (a) an MDM4-antagonist and (b) one or more chemotherapeutic agents.

In a yet further aspect, provided is a pharmaceutical preparation comprising: (a) an MDM4-antagonist; and (b) one or more chemotherapeutic agents, together with a pharmaceutically acceptable carrier.

In preferred embodiment, provided is a pharmaceutical preparation comprising: (a) an MDM4-antagonist; and (b) one or more chemotherapeutic agents selected from a microtubule active agent; an alkylating agent; an anti-neoplastic anti-metabolite; a platin compound; a topoisomerase I inhibitor, a topoisomerase II inhibitor; a VEGF inhibitor; a tyrosine kinase inhibitor; an EGFR kinase inhibitor; an mTOR kinase inhibitor; an insulin-like growth factor I inhibitor; a Raf kinase inhibitor; a PI3/AKT inhibitor, a MEK kinase inhibitor, a proteasome inhibitor; a HDAC inhibitor; and ionizing radiation.

Any of the combination of components (a) and (b), the method of treating a human comprising administering these two components, a pharmaceutical composition comprising these two components for simultaneous, separate or sequential use, the use of the combination for the delay of progression or the treatment of melanoma, in particularly cutaneous melanoma, or metastatic melanoma, or for the manufacture of a pharmaceutical preparation for these purposes or a commercial product comprising such a combination of components (a) and (b), all as mentioned or defined above, will be referred to subsequently also as "combinations herein described" (so that this term refers to each of these embodiments, which thus can replace this term where appropriate).

Simultaneous administration may, e.g., take place in the form of one fixed combination with two or more active ingredients, or by simultaneously administering two or more active ingredients that are formulated independently. Sequential use (administration) preferably means administration of one (or more) components of a combination at one time point, other components at a different time point, that is, in a chronically staggered manner, preferably such that the combination shows more efficiency than the single compounds administered independently (especially showing synergism). Separate use (administration) preferably means administration of the components of the combination independently of each other at different time points. Also combinations of two or more of sequential, separate and simultaneous administration are possible, preferably such that the combination component-drugs show a joint therapeutic effect that exceeds the effect found when the combination component-drugs are used independently at time intervals so large that no mutual effect on their therapeutic efficiency can be found, a synergistic effect being especially preferred.

Determining a synergistic interaction between one or more components, the optimum range for the effect and absolute dose ranges of each component for the effect may be definitively measured by administration of the components over different w/w ratio ranges and doses to patients in need of treatment. For humans, the complexity and cost of carrying out clinical studies on patients renders impractical the use of this form of testing as a primary model for synergy. However, the observation of synergy in one species can be predictive of the effect in other species and animal models exist, as described herein, to measure a synergistic effect and the results of such studies can also be used to predict effective dose and plasma concentration ratio ranges and the absolute doses and plasma concentrations required in other species by the application of pharmacokinetic/pharmacodynamic methods. Established correlations between tumor models and effects seen in humans suggest that synergy in animals may, e.g., be demonstrated in the melanoma tumor model as described in the examples below.

The term "delay of progression," as used herein, means administration of the combination to patients being in a pre-stage or in an early phase of melanoma, of the first or subsequent manifestations; or a relapse of the melanoma to be treated in which patients, e.g., a pre-form of the corresponding disease is diagnosed; or which patients are in a condition, e.g., during a medical treatment.

"Jointly therapeutically active" or "joint therapeutic effect" means that the compounds may be given separately (in a chronically staggered manner, especially a sequence-specific manner) in such time intervals that they preferably, in the human, to be treated, still show a (preferably synergistic) interaction (joint therapeutic effect).

"Pharmaceutically effective" preferably relates to an amount that is therapeutically or in a broader sense also prophylactically effective against the progression of melanoma, particularly subcutaneous melanoma, particularly metastatic melanoma.

A pharmaceutical product, as used herein, defines especially a "kit of parts" in the sense that the components (a), which is the MDM4-inhibitor and (b), which includes one or more chemotherapeutic agents, as defined above, can be dosed independently or by use of different fixed combinations with distinguished amounts of the components (a) and (b), i.e., simultaneously or at different time points. Moreover, these terms comprise a commercial package comprising (especially combining) as active ingredients components (a) and (b), together with instructions for simultaneous, sequential, chronically staggered, in time-specific sequence, preferentially) or (less preferably) separate use thereof in the delay of progression or treatment of melanoma, particularly subcutaneous melanoma, particularly metastatic melanoma.

The parts of the kit of parts can then, e.g., be administered simultaneously or chronologically staggered, that is at different time points and with equal or different time intervals for any part of the kit of parts. Very preferably, the time intervals are chosen such that the effect on the treated melanoma in the combined use of the parts is larger than the effect that would be obtained by use of only any one of the combination partners (a) and (b) as can be determined according to standard methods. The ratio of the total amounts of the combination partner (a) to the combination partner (b) to be administered in the combined preparation can be varied, e.g., in order to cope with the needs of a patient sub-population to be treated or the needs of the single patient, which different needs can be due to the particular disease, age, sex, body weight, etc., of the patients. Preferably, there is at least one beneficial effect, e.g., a mutual enhancing of the effect of the combination partners (a) and (b), in particular, a more than additive effect, which hence could be achieved with lower doses of each of the combined drugs, respectively, than tolerable in the case of treatment with the individual drugs only without combination, producing additional advantageous effects, e.g., less side effects or a combined therapeutic effect in a non-effective dosage of one or both of the combination partners (components) (a) and (b), and very preferably a strong synergism of the combination partners (a) and (b).

In a particular embodiment, the "combinations herein described" can also be applied in combination with other treatments, e.g., surgical intervention, hyperthermia and/or irradiation therapy.

In yet another embodiment, provided is a pharmaceutical composition comprising i) an MDM4-inhibitor and ii) one or more chemotherapeutic agents selected from a microtubule active agent, an alkylating agent, an anti-neoplastic anti-metabolite, a platin compound, a Raf kinase inhibitor, a MEK kinase inhibitor, a topoisomerase I inhibitor, a topoisomerase II inhibitor, a VEGF inhibitor, a tyrosine kinase inhibitor, an EGFR kinase inhibitor, an mTOR kinase inhibitor, a PI3/AKT inhibitor, an insulin-like growth factor I inhibitor, a HDAC inhibitor, a proteasome inhibitor.

In yet another embodiment, provided is a pharmaceutical composition comprising i) an MDM4-inhibitor and ii) one or more chemotherapeutic agents selected from camptothecin derivatives, paclitaxel, docetaxel, melphalan, temozolomide, cacarbazine, epothilone B, 5-FU, gemcitabine, oxaliplatin, cisplatinum, carboplatin, melphalam, doxorubicin, imatinib, erlotinib, bevacizumab, cetuximab and a Raf kinase inhibitor.

In yet another embodiment, provided is a pharmaceutical composition comprising i) an MDM4-inhibitor and ii) one or more chemotherapeutic agents selected from oxaliplatin, cisplatinum, carboplatin, melphalam, dacarbazine, temozolomide and a RAF kinase inhibitor.

In yet another embodiment, provided is a pharmaceutical composition comprising i) an MDM4-inhibitor and ii) a RAF kinase inhibitor.

The pharmaceutical compositions provided herein can be prepared by conventional means and are those suitable for enteral, such as oral or rectal, and parenteral administration to mammals including man, comprising a therapeutically effective amount of an MDM4 inhibitor and at least one chemotherapeutic agent alone or in combination with one or more pharmaceutically acceptable carriers, especially those suitable for enteral or parenteral application.

The pharmaceutical compositions comprise from about 0.00002% to about 100%, especially, e.g., in the case of infusion dilutions that are ready for use) of 0.0001-0.02%, or, e.g., in case of injection or infusion concentrates or especially parenteral formulations, from about 0.1% to about 95%, preferably from about 1% to about 90%, more preferably from about 20% to about 60%, active ingredient (weight by weight, in each case). Pharmaceutical compositions may be, e.g., in unit dose form, such as in the form of ampoules, vials, dragees, tablets, infusion bags or capsules.

The effective dosage of each of the combination partners employed in a formulation may vary depending on the particular compound or pharmaceutical compositions employed, the mode of administration, and the stage of the melanoma being treated. A physician, clinician or veterinarian of ordinary skill can readily deter mine the effective amount of each of the active ingredients necessary to prevent, treat or inhibit the progress of the melanoma.

Pharmaceutical preparations for the combination therapy for enteral or parenteral administration are, e.g., those in unit dosage forms, such as sugar-coated tablets, capsules or suppositories; and furthermore ampoules. If not indicated otherwise, these formulations are prepared by conventional means, e.g., by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units. One of skill in the art has the ability to determine appropriate pharmaceutically effective amounts of the combination components.

Preferably, the compounds or the pharmaceutically acceptable salts thereof, are administered as an oral pharmaceutical formulation in the form of a tablet, capsule or syrup; or as parenteral injections if appropriate.

In preparing compositions for oral administration, any pharmaceutically acceptable media may be employed, such as water, glycols, oils, alcohols, flavoring agents, preservatives or coloring agents. Pharmaceutically acceptable carriers include starches, sugars, microcrystalline celluloses, diluents, granulating agents, lubricants, binders and disintegrating agents.

Solutions of the active ingredient, and also suspensions, and especially isotonic aqueous solutions or suspensions, are useful for parenteral administration of the active ingredient, it being possible, e.g., in the case of lyophilized compositions that comprise the active ingredient alone or together with a pharmaceutically acceptable carrier, e.g., mannitol, for such solutions or suspensions to be produced prior to use. The pharmaceutical compositions may be sterilized and/or may comprise excipients, e.g., preservatives, stabilizers, wetting and/or emulsifying agents, solubilizers, salts for regulating the osmotic pressure and/or buffers, and are prepared in a manner known per se, e.g., by means of conventional dissolving or lyophilizing processes. The solutions or suspensions may comprise viscosity-increasing substances, such as sodium carboxymethylcellulose, carboxymethylcellulose, dextran, polyvinylpyrrolidone or gelatin. Suspensions in oil comprise as the oil component the vegetable, synthetic or semisynthetic oils customary for injection purposes.

The isotonic agent may be selected from any of those known in the art, e.g., mannitol, dextrose, glucose and sodium chloride. The infusion formulation may be diluted with the aqueous medium. The amount of aqueous medium employed as a diluent is chosen according to the desired concentration of active ingredient in the infusion solution. Infusion solutions may contain other excipients commonly employed in formulations to be administered intravenously, such as antioxidants.

In a particular embodiment provided is a method for testing the eligibility of a patient suffering from melanoma, or cutaneous melanoma, or metastatic melanoma, for treatment with an MDM4 inhibitor comprising determining the protein expression level of MDM4 in a melanoma tumor sample derived from the patient and wherein an enhanced MDM4 protein expression compared to the MDM2 protein expression selects the patient as eligible for treatment. In other words, provided for is a companion diagnostic for testing the eligibility of a patient suffering from melanoma for treatment with an MDM4 inhibitor or a pharmaceutical composition comprising an MDM4 inhibitor.

In yet another embodiment, provided is a method for testing the eligibility of a patient suffering from melanoma for treatment with a pharmaceutical composition of a combination between an MDM4-inhibitor and one or more chemotherapeutic agents as described before comprising determining the protein expression level of MDM4 and determining the B-RAF status in a melanoma tumor sample derived from the patient and wherein an enhanced MDM4 protein expression compared to the MDM2 protein expression and the presence of a B-RAF activating mutation selects the patient as eligible for treatment.

The term "B-RAF status" means that the B-RAF gene is screened for the presence of B-RAF activating mutations, in particular for the presence of the B-RAF mutation, B-RAF$^{V600E}$ Determination of the B-RAF status typically comprises PCR amplification of the B-RAF nucleotide sequence derived from a tumor sample and determining the nucleotide sequence of the B-RAF amplified nucleotide sequence.

A "melanoma tumor sample derived from a patient" typically means a tissue biopsy derived from a melanoma present in a patient. The term "an enhanced MDM4 protein expression compared to the MDM2 protein expression" refers to the ratio between the MDM4 protein expression level and the MDM2 protein expression level, which ratio is typically higher than 1, higher than 2, higher than 3, higher than 4 or even higher than 5. The absence of MDM4 protein expression means that the patient is not eligible for treatment with the pharmaceutical compositions.

One of the merits of the embodiments herein is that it was found that the protein expression levels of MDM4 and MDM2 were mutually exclusive (an exception being only a low fraction of metastatic melanomas where the protein expression levels of MDM4 and MDM4 were found high; it is submitted that also the latter group is eligible for treatment with the pharmaceutical compositions). In a particular embodiment the protein expression level of MDM2 is absent or not detectable in the melanoma biopt. Indeed, we have found that in most cases of melanoma the protein expression level of MDM2 is non-detectable or very low. In yet another embodiment the protein expression level of MDM4 in a suspected melanoma biopt is quantified as compared to the protein expression level of MDM4 in benign congenital melanocytic nevi. In these benign congenital melanocytic nevi we observed that the MDM4 protein expression level was very low. Hence, a high ratio of MDM4 protein expression level (biopt versus benign congenital melanocytic levi), which is preferably higher than 2, 3, 4, 5, 6, 7, 8, 9, 10 or more, also means that the patient is eligible for treatment with the pharmaceutical compositions.

The determination of the protein expression level of MDM2 and the protein expression level of MDM4 can be carried out with a number of methods described in the art for determining the protein expression level. Non-limiting examples are antibody based methods for the detection and quantification of MDM4 and MDM2 such as western blot analysis, ELISA, immunoblotting, immunoelectrophoresis, immunoprecipitation. Antibodies that can be used are monoclonal or polyclonal antibodies directed against MDM4 or MDM2. Yet another method to detect and quantify the ratio between MDM4 and MDM2 protein expression levels is the proximity ligation assay (see, for example, Söderberg, Ola et al. (2006), "Direct observation of individual endogenous protein complexes in situ by proximity ligation," *Nature Methods* 3 (12):995-1000.

The following Examples illustrate the invention described above; they are not, however, intended to limit the scope of the invention in any way. The beneficial effects of the pharmaceutical compositions can also be determined by other test models known as such to the person skilled in the pertinent art.

EXAMPLES

Example 1

MDM4 is Over Expressed in 60% of Human Melanomas

In most human melanoma cell lines p53 is wild-type and highly expressed, but transcriptionally inactive.[26] Since MDM4 overexpression stabilizes p53 by competing with MDM2 for p53 binding and inhibits p53 transcriptional activity[24] we hypothesized that MDM4 overexpression might contribute to inactivation of p53 in melanomas. Although we have previously found MDM4 amplification in retinoblastoma and breast cancer[27, 28] we did not find evidence for an increased somatic copy-number of MDM4 in melanomas through in silico analysis.[29, 30] Meta-analysis of Oncomine microarray data (Oncomine 4.4 Research Edition; www.oncomine.org) failed to identify any significant or recurrent up-regulation of MDM4 mRNA expression in melanomas. We nevertheless assessed MDM4 levels in a panel of 40 primary skin melanomas: ten primary, non-invasive, ten regional dermal metastases, ten nodal metastatic lesions and ten distant metastatic lesions. Consistent with the in silico data, the large majority of these samples (36/40) expressed MDM4 mRNA levels that were lower than in MCF-7 a cell line expressing relatively high MDM4 levels.[27] In contrast, MDM4 protein levels were considerably higher than in MCF-7 in ~60% of cases (FIG. 1A). Whereas MDM4 protein expression was barely detectable in benign congenital melanocytic nevi (CN), high MDM4 protein levels were already evident in many of the primary, non-invasive, tumor samples (6/10) indicating that MDM4 protein up-regulation is an early event during melanomagenesis. In contrast, MDM2 protein levels ranged from non-detectable to low in the majority of cases. High MDM2 levels were only found in a few metastatic lesions: 1/10 regional dermal, 1/10 nodal and 4/10 distant metastatic lesions (FIG. 1A). Overexpression of MDM2 and MDM4 was mutually exclusive, except in 2/10 (samples 33 and 37) metastatic melanomas. p53 levels varied from sample to sample and were only very high in two samples (samples 23 and 24). As mutant p53 is often expressed at very high levels this observation raises the possibility that p53 is only mutated in these two particular samples (FIG. 1A), an observation that is consistent with the previously reported low mutation rate of p53 in melanoma.[14, 26]

MDM4 protein overexpression was further confirmed in a panel of human metastatic melanoma (MM) cell lines. MDM4 protein levels were very high in 8 (MM001, MM011, MM031, MM032, MM047, MM057, MM117, MM120) out of 17 patient-derived short-term cultures established from metastatic tumors and in all (4/4) commonly used cell lines harboring wild-type p53 (A375, WM9, MeI-501, Lu1205) (FIG. 1B). Importantly, MDM4 protein was not detectable in normal primary melanocyte cultures. In addition to the very high expressers, MDM4 protein levels were also higher than in normal melanocytes in 6 (MM029, MM034, MM061, MM074, MM087, MM118) of 17 cell lines; hence, overall MDM4 protein levels were elevated in 14 out of the 17 lines compared to primary melanocytes. Consistent with a post-transcriptional mechanism being responsible for MDM4 up-regulation, MDM4 mRNA levels were only significantly elevated in one of the 17 short-teen cultured cell lines (MM120). As in the primary melanoma samples, MDM2 protein levels in the short-term cultures ranged from non-detectable to low in the majority of cases and were only high in four cases (MM011, MM034, MM061, MM117) and very high in two cases (MM001, MM120). Notably, MDM2 protein expression levels were very high in all (4/4) well-established melanoma cell lines, a situation that could be a consequence of extensive in vitro passaging of these cells.

Finally, all the MM cell lines expressed relatively high levels of p53. To test whether the p53 tumor suppressor response was intact downstream of MDM4 we exposed most of the short-term cultured cell lines to the DNA-damaging agent doxorubicin (Doxo) and to high concentrations of the MDM2 antagonist nutlin-3.[31] All but one (MM87) of the cell lines overexpressing MDM4 had an intact p53 pathway as evidenced by increased p53 protein levels and induction of expression of p21, an established p53-transcriptional target.[32] p53 stabilization and concomitant induction of p21 was also observed in response to these treatments in two of the commonly used cell lines analyzed (A375, and Lu1205).

BRAF and NRAS mutational status was determined in all primary tumors and cell lines described above. MDM4 overexpression was observed at comparable frequencies in tumors and cell lines harboring either wild-type or NRAS or BRAF mutations indicating that MDM4 overexpression is independent of the BRAF and NRAS mutational status.

Hence, MDM4 protein, but not mRNA, is frequently over expressed at very high levels in human primary melanoma tumors and metastatic melanoma cell lines. Observing MDM4 protein overexpression already in the non-invasive, non-metastatic, melanomas may indicate a significant role for this oncogene in early melanocyte transformation. Collectively, our results indicate that MDM4 protein up-regulation is an important driving oncogenic event and a key mechanism that contributes to p53 inactivation during melanomagenesis.

Example 2

Inhibition of the MDM4-p53 Interaction Restores p53 Activity in Melanoma

Figure 2A:
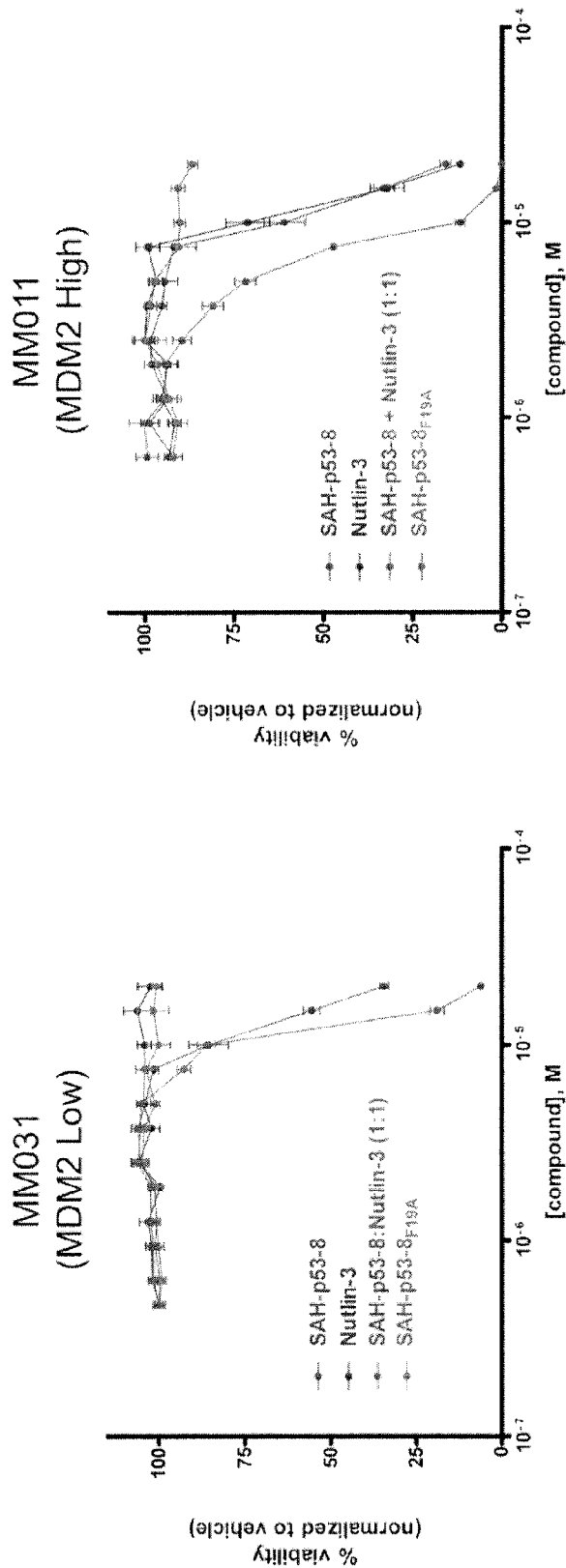
FIG. 2: Inhibition of the MDM4-p53 interaction restores p53 activity in melanoma. (A) Viability of MM031 (left) and MM011 (right) melanoma cell lines treated with 0.5-20 mM SAH-p53-8, Nutlin-3, or an equimolar combination for 24 hours. The cells were exposed to CellTiter-Glo reagent and viability was assessed by ATP induced chemiluminescence. Data are mean±SD for experiments performed in at least triplicate. (B) Dose-effect synergy analyses of MM031 (left) and MM011 (right) and melanoma cells treated with 0.5-20 μM SAH-p53-8, Nutlin-3, or an equimolar combination. The $EC_{50}$ values for each of the treatments are indicated. (C) RT-qPCR mRNA expression analysis of selected p53 target genes in melanoma cell lines 24 hours post SAH-p53-8 treatment ($EC_{50}$ of SAH used per each cell line); SAH-p53-8$_{F19A}$ was used as a point mutant control and DMSO as a vehicle control. The data represent the mean (±SD) from three technical triplicates. The values are normalized to the level of mRNA expression in vehicle-treated cells. (D) SAH-p53-8 overcomes MDM4-mediated p53 suppression and blocks tumor growth in vivo. (Left) Cohorts of MM031 xenograft mice were treated with vehicle (5% DMSO in D5W) or 10 mg/kg of SAH-p53-8 by intravenous injection daily for five consecutive days and tumor volume was monitored by caliper measurement daily for a period of twelve days. Data represent the mean (±SD) of 7 different biological replicates (P<0.005 on day 12). (Right) External views of representative tumor-bearing mice on day 12.

The reliance of melanoma on MDM4 for survival suggests that antagonizing its interaction with wild-type p53 should restore p53-driven pro-apoptotic activities in melanoma cells. Recently, Bernal and co-workers described the design, synthesis and evaluation of stabilized alpha helical peptides (SAH) based on the transactivation domain of p53.[39] One of these compounds, SAH-p53-8, binds directly MDM4 within its p53-binding pocket with high affinity and is capable of disrupting p53-MDM4 complexes in vitro and in vivo.[40] In contrast to nutlin-3, this compound is capable of reactivating the p53 tumor suppressor functions and induce apoptosis in cells with high levels of wild-type p53 and MDM4.[40] To test whether direct inhibition of MDM4 is a viable therapeutic strategy for melanoma we treated the MM cell lines with SAH-p58-8, its biologically inactive point mutant analog SAH-p53-8$_{F19A}$, the MDM2-specific inhibitor nutlin-3, or a 1:1 stoichiometric combination of both SAH-p53-8 and nutlin-3 (FIG. 2A). As expected since the MM031 cells express low levels of MDM2 and high levels of MDM4, nutlin-3 had only a marginal cytotoxic effect on these cells. In sharp contrast, MM031 exhibited robust growth inhibition in response to SAH-p53-8 alone, and there was only a very modest increase in cytotoxicity upon combination with nutlin-3 (FIG. 2B left panel; Combination Index CI=0.90).

Figure 2B:
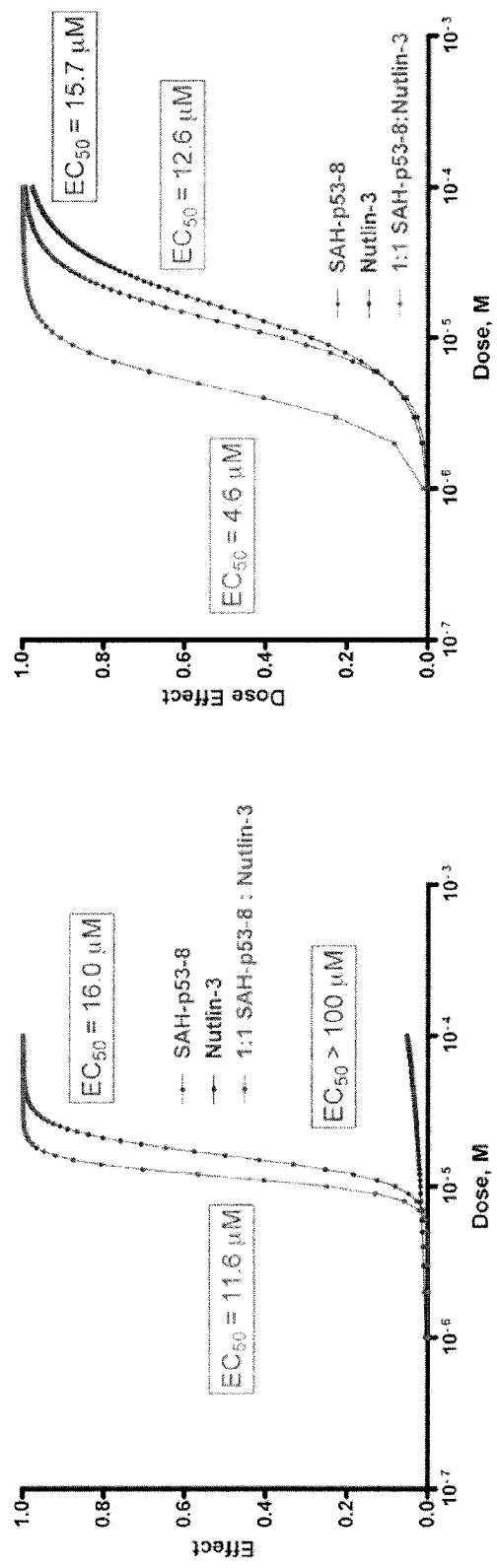
Figure 2C:
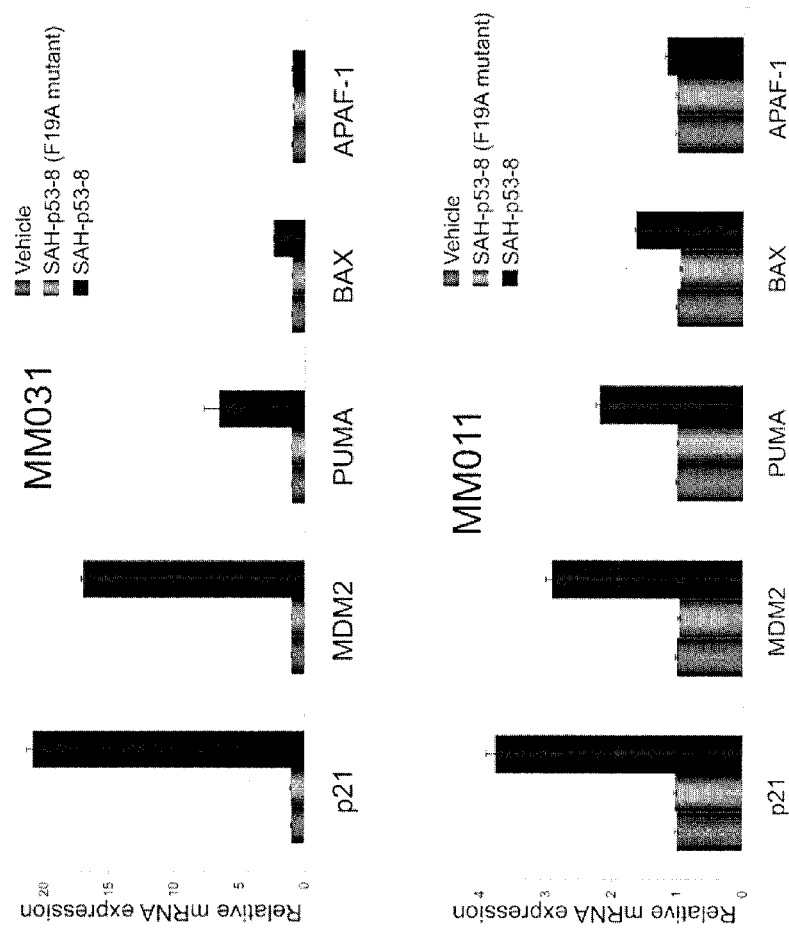

Consistent with previous work,[40] the MM011 cells that express high levels of both MDM4 and MDM2 showed sensitivity to the single agents SAH-p53-8 and nutlin-3 (FIG. 2A, right panel). Most notably, these two compounds synergize strongly with one another displaying enhanced cytotoxicity over the single treatment regimen (FIG. 2B, right; combination index CI=0.32). Similar effects were observed in the conventional melanoma cell line Lu1205, which expresses both MDM4 and MDM2 at high levels (data not shown). As further demonstration of specificity, the mutant SAH-p53-8$_{F19A}$ peptide did not induce any measurable cytotoxic effects in any of the melanoma cell lines. Together our data indicate that all human melanoma cell lines are highly sensitive to MDM4 inhibition alone or in combination with MDM2 inhibition. RT-qPCR analyses further confirmed the ability of SAH-p53-8, but not SAH-p53-8$_{F19A}$, to induce expression of a series of established p53-target genes in all melanoma cell lines analyzed (FIG. 2C).

Figure 2D:
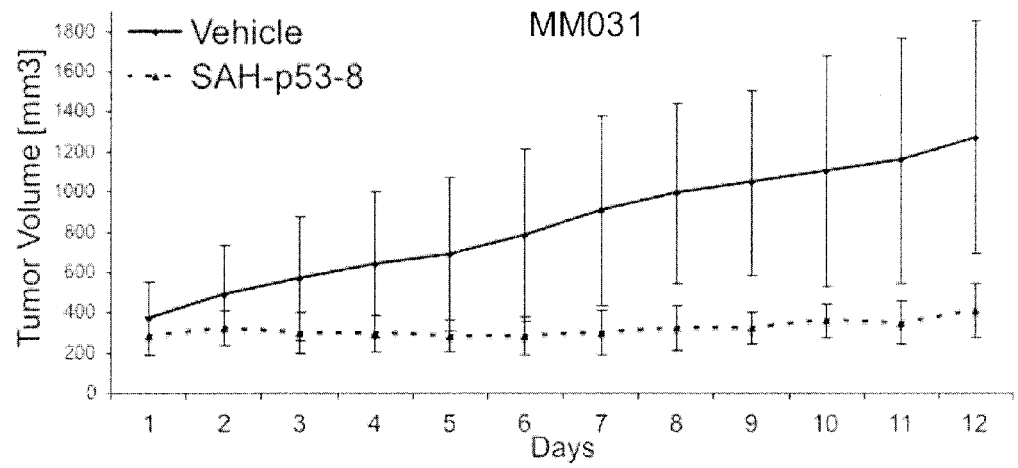
Figure 2D:
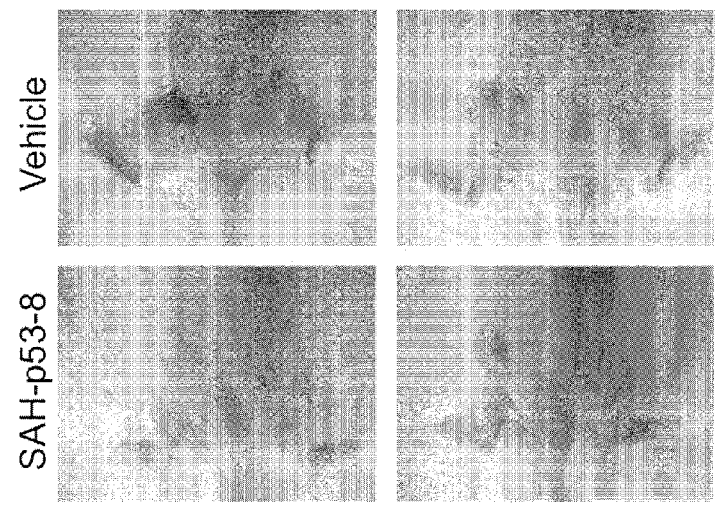

To test the therapeutic potential of inhibiting the p53-MDM4 interaction on melanoma progression in vivo we compared the activity of vehicle and SAH-p53-8 in a MM031 murine xenograft model. MM031 xenografts were established by subcutaneous injections into the flanks of immunocompromised mice. When tumors reached an average volume of 200 mm³, cohorts were treated intravenously with vehicle or SAH-p53-8 daily for five consecutive days. Whereas tumor growth rate was unaffected in vehicle-treated mice, treatment with SAH-p53-8 significantly suppressed tumor growth throughout the ten-day evaluation period (FIG. 2D). As previously shown, histological examination of SAH-p53-8-treated mice showed no obvious toxicity of the compound to normal tissues.[40] Collectively, these data highlight the pharmacologic potential of existing MDM4 inhibitors for the treatment of melanoma.

Example 3

Targeting the MDM4-p53 Pathway Sensitizes Melanoma to Conventional Chemotherapy

Figure 3A:
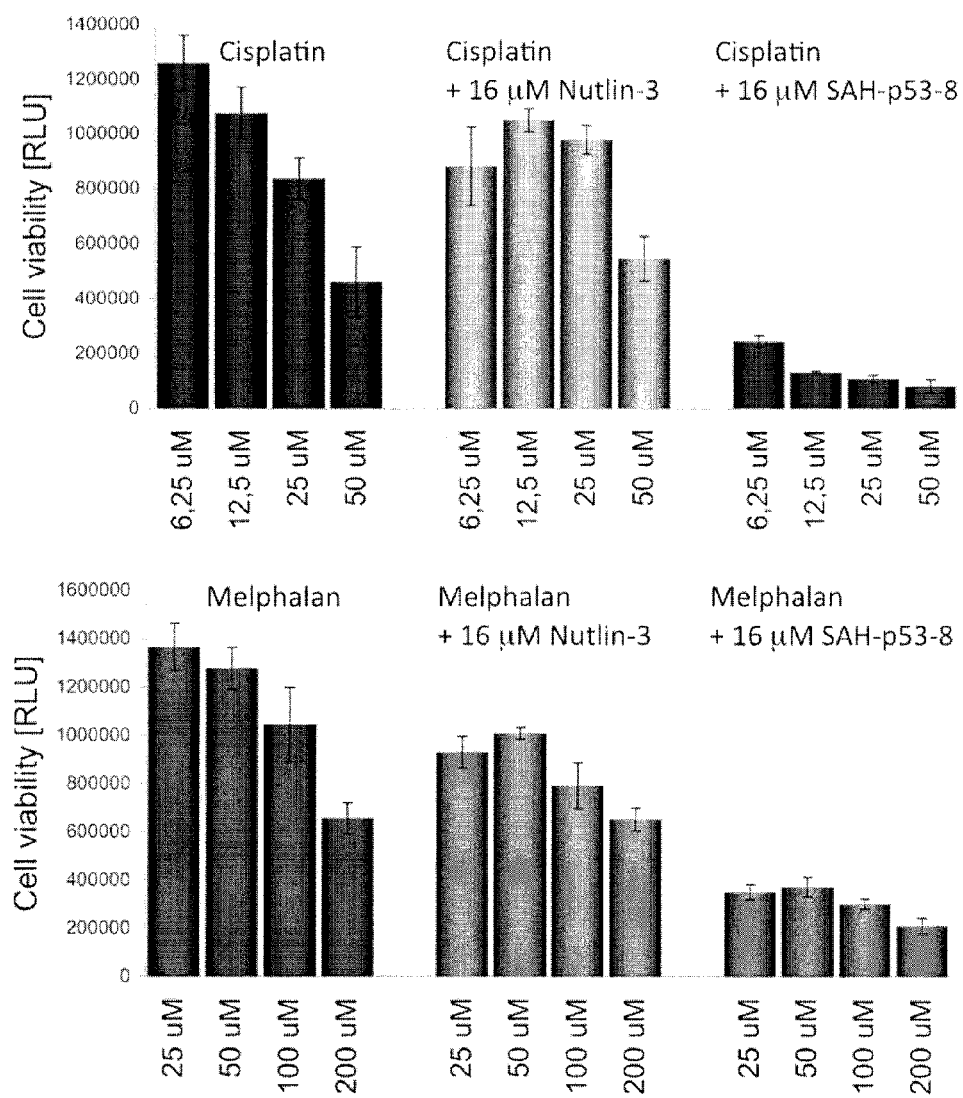
FIG. 3: Therapeutic potential of targeting the MDM4-p53 pathway. (A) and (B) Targeting the MDM4-p53 interaction sensitizes metastatic melanoma cells to chemotherapy. MM031 (A) and MM011 (B) melanoma cells were treated with 6.25-50 μM Cisplatin or 25-200 μM Melphalan with or without $EC_{50}$ dose of SAH-p53-8 or with or without corresponding dose of nutlin-3. (B) Dose effect synergy analyses of MM011 melanoma cells treated with 6.25-50 μM cisplatin with or without 0.5-20 μM SAH-p53-8 or nutlin-3. Cell viability was measured at 24 hours by CellTiter-Glo assay. Data represent the mean (±SD) of at least three biological replicates. (C) Targeting the MDM4-p53 pathway sensitizes melanoma cells to a $BRAF^{V600E}$-inhibitor. BRAF-resistant and parental cell lines were exposed to increasing doses of SAH-p53-8 (10-40 μM). Cell viability was measured by Cell-Titer-Glo assay at 24 hours post SAH-p53-8 treatment. Data represent the mean (±SD) of at least three biological replicates. (D) Dose-effect synergy analyses of melanoma cells treated with 5 μM PLX4032 and an $EC_{50}$ dose of SAH-p53-8 (18 μM). Data represent the mean (±SD) of at least three biological replicates.
Figure 3B:
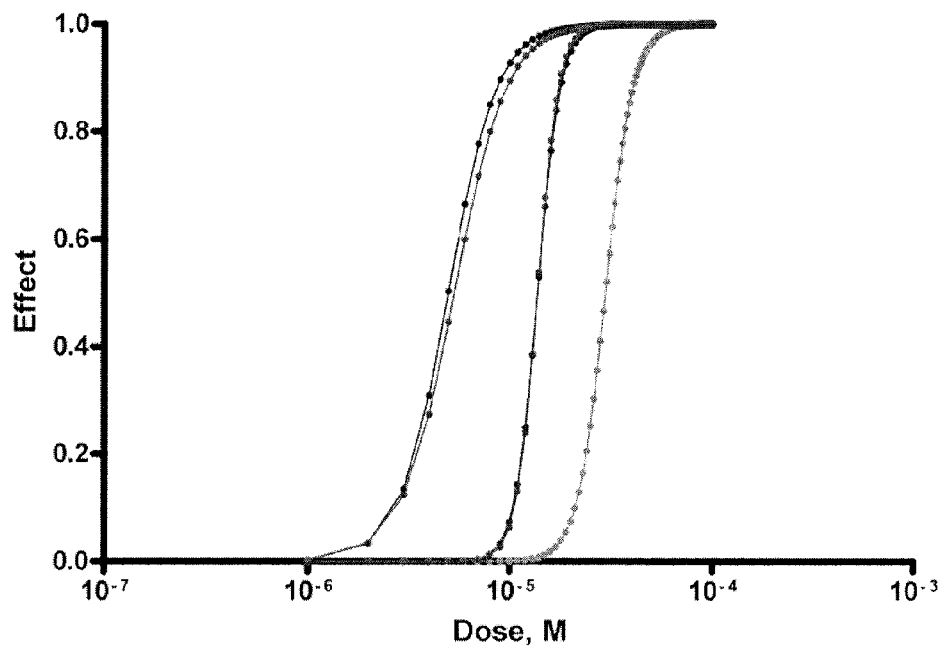

The use of DNA-damaging agents such as cisplatin or melphalan in the clinic has yielded low response rates in melanoma, of which few are durable.[41] Strategies that increase the sensitivity of melanoma cells to genotoxic agents are expected to decrease their toxicity and eventually improve their potency. Since the effectiveness of these agents relies on the reactivation of a genetically uncompromised p53 pathway, we hypothesized that combination treatment with p53-MDM4 inhibitors would enhance cytotoxicity caused by DNA-damaging agents. To test this possibility, we investigated the effects of cisplatin and melphalan alone or in combination with nutlin-3 or SAH-p53-8 on the growth of the MM011 and MM031 cell lines. Treatment of these cells with cisplatin or melphalan alone yielded variable growth inhibition effects (FIGS. 3A and 3B). Importantly, the cytotoxic effects of these alkylating agents were greatly potentiated by co-treatment with SAH-p53-8. Because they express low levels of MDM2 and consistent with our mechanistic hypothesis, MM031 cells responded more favorably to the combination of cisplatin or melphalan with SAH-p53-8 than co-treatment with nutlin-3 (FIG. 3A). On the other hand, the high levels of MDM2 in MM011 cells render SAH-p53-8 as effective as nutlin-3 in synergizing with cisplatin (FIG. 3B). These data demonstrate that targeting the MDM4-p53 axis significantly sensitizes metastatic melanoma cells to DNA-damaging agents.

Example 4

Targeting the MDM4-p53 Axis Kills BRAF Inhibitor-Resistant Melanoma Cells

Figure 3C:
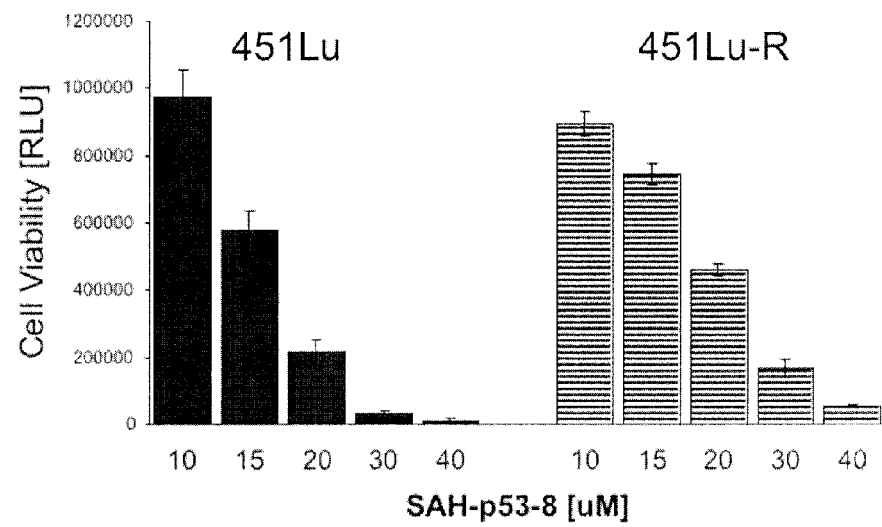
Figure 3C:
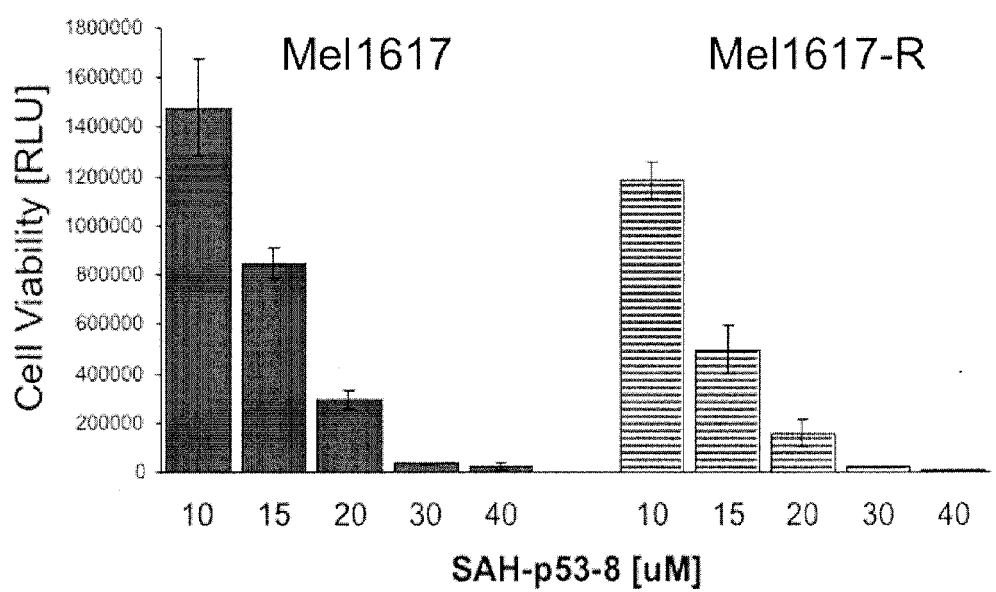
Figure 3D:
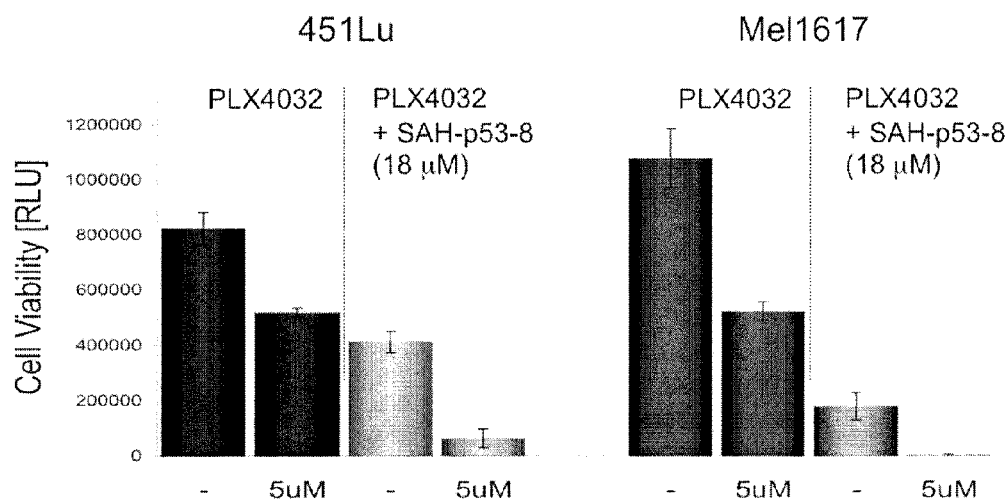

Chronic treatment with BRAF inhibitors is invariably associated with the development of drug resistance.[42] Overcoming BRAF inhibitor resistance is likely to require targeting of multiple signaling pathways. Since MDM4 overexpression was observed in tumors irrespective of BRAF mutational status, we investigated whether targeting the MDM4-p53 interaction could affect the growth of BRAF inhibitor-sensitive parental melanoma cell lines (451Lu and Mel1617) as well as BRAF-resistant sub-lines (451Lu-R and Mel1617-R), which were artificially derived by chronic exposure to a BRAF inhibitor.[43] Strikingly, treatment of both parental and BRAF-resistant cell lines with increasing doses of SAH-p53-8 led to decreased viability, indicating that cells that have acquired drug resistance to BRAF inhibitor remain sensitive to MDM4-p53 targeting (FIG. 3C). To investigate whether combined BRAF and MDM4 inhibition synergizes to induce cytotoxic effects we treated BRAF inhibitor-sensitive lines with a BRAF-inhibitor, PLX4032, and SAH-p53-8 as single agents or in combination. As expected, exposure to PLX4032 alone was sufficient to induce a significant decrease in cell viability (FIG. 3D). More significantly simultaneous treatment with PLX4032 and SAH-p53-8 greatly enhanced the effect when compared with each individual compound (FIG. 3D). The collective data show that co-targeting of MDM4 and mutant BRAF results in potent anti-tumor activity in melanomas harboring BRAF mutations, and may, therefore, offer a novel therapeutic avenue for limiting and overcoming the resistance to BRAF inhibitors. Additionally, as melanoma cells, that acquire resistance to BRAF inhibitors, remain addicted to high protein levels of MDM4, targeting the MDM4-p53 pathway is a valid therapeutic approach to treat relapsed patients.

Example 5

MDM4 Protein Overexpression in Dysplastic Nevi

Example 1 shows that the protein MDM4 is over expressed in more than 60% of the late stage human melanomas. In the present example we investigated the whether the MDM4 protein overexpression could be used as a diagnostic aid for differentiating benign melanocytic nevi from dysplastic melanocytic nevi. Melanocytic nevi are benign tumors of melanocytes but nevi are considered as the most important stimulants of melanoma. In particular, dysplastic nevi are considered to be the most precursors of melanoma and it is important to be able to distinguish between benign and dysplastic melanocytic nevi. Fifty samples of benign melanocytic nevi and 50 samples of dysplastic melanocytic nevi were investigated for the expression of the protein MDM4. Our data show that the MDM4 protein is not expressed in benign nevi but that the expression of the MDM4 protein occurs in more than 50% of dysplastic nevi.

Example 6

AKT Inhibitors Down-Regulate MDM4 Protein Levels in Melanomas

Figure 4:
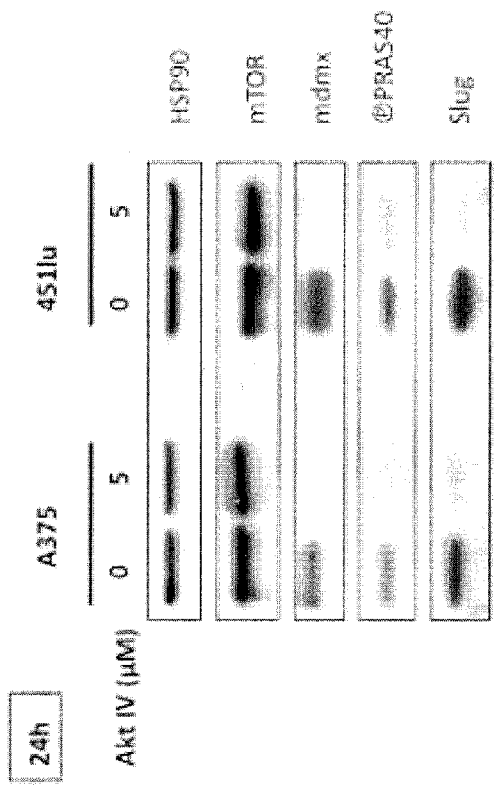
FIG. 4: AKT inhibitors destabilize the MDM4 protein levels in melanomas. The figure shows that 5 μM of Akt IV applied for 24 hours on human melanoma cell lines A375 and 451-lu down-regulates (or destabilizes) the MDM4 protein.

In the present example we applied the Akt IV inhibitor on two different melanoma cell lines (i.e., the human amelanotic melanoma cell line A375 and the metastatic 451-lu human melanoma cell line, the latter also described in D. Herlyn et al. (1990), *Cancer Research* 50, 2296-2302). Our data show that 5 µM of the Akt IV inhibitor (CAS number 681281-88-9, purchased at Calbiochem) down-regulate the protein expression level of MDM4 in these two human melanoma cell lines (see FIG. 4).

Materials and Methods

1. Reagents

The stapled peptides SAH-p53-8 and SAH-p53-8$_{F19A}$ were obtained from Dr. Federico Bernal, National Cancer Institute, CCR, Metabolism Branch, Rockville, Md. 20852. PLX4032 (also known as vemurafenib or RG7204 or RO5185426) was purchased from Selleck Chemicals. Before application 10 mg of PLX4032 was suspended in DMSO at a concentration of 2.5 mM.

2. Melanoma Cell Cultures

The panel of 40 primary skin melanomas was kindly provided by the Institute Jules Bordet, Brussels, Belgium. The panel of human metastatic melanoma (MM) cell lines was kindly provided by the UMDNJ-Robert Wood Johnson Medical School, CINJ, NJ, US. Human melanoma cell lines MM001, MM011, MM031, MM117, were cultured in F10 medium with 5% fetal bovine serum (HyClone), 5% calf bovine serum (HyClone) and antibiotics. A375 and Lu1205 melanoma cell lines were cultured in respectively RPMI and DMEM medium with 10% fetal bovine serum (Sigma) and antibiotics. 451Lu, 451Lu-R, Mel1617 and Mel1617-R cell lines were kindly provided by M. Herlyn (The Wistar Institute, Philadelphia, US), these cell lines were cultured in DMEM plus 5% fetal bovine serum (HyClone) and antibiotics. The resistant cells were maintained in 1 μM BRAF inhibitor PLX4032, supplemented every 72 hours.

3. Cell Growth and Viability

Cell growth was measured using the WST-1 assay (Roche). Cells were counted and seeded in triplicate in 96-well plates at a density of 3000 or 6000 cells per well, in a total volume of 100 μl. medium. Cells were incubated with 10 μl WST-1 reagent for 2 hours and absorbance (450 nm) was measured in a microplate reader (Victor; Perkin Elmer).

Alternatively, cell growth was measured using the CellTiter-Glo Assay (Promega). Cells were counted and seeded in triplicate in 96-well plates at a density of 15,000 cells per well, and treated with chemotherapeutics: cisplatin (Sigma) or melphalan (Sigma), SAH-p53-8 and SAH-p53-$8_{F19A}$ (both synthesized and characterized in the Bernal laboratory, NCI),[40] BRAF inhibitor (PLX4032, Roche) or nutlin-3 (Johnson & Johnson) for 24 hours after which the CellTiter-Glo reagent was added to the cells in a 1:1 ratio. Luminescence was measured in a microplate reader (Victor; Perkin Elmer).

4. Apoptosis Assays

Apoptosis was measured using the Caspase-Glo 3/7 Assay (Promega). Cells were counted and seeded in triplicate in 96-well plates at a density of 12,000 cells per well. Next day the Caspase-Glo 3/7 reagent was added to the cells in a 1:1 ratio. Luminescence was measured in a microplate reader (Victor; Perkin Elmer) after 1 h shaking at RT.

5. Colony Formation Assays

Cells were plated at a density between $2 \times 10^3$ and $32 \times 10^3$ cells per 6-well plate and cultured for 12 days. The cells were then washed with PBS 1×, fixed and stained 5 minutes with a 1% crystal violet in 35% methanol solution.

6. Western Blotting Analysis

Cells, adult tissue samples, or tumors were lysed in Giordano buffer (50 mM Tris-HCl (pH 7.4); 250 mM NaCl; 0.1% Triton X-100; 5 mM EDTA) containing phosphatase and protease inhibitors (Sigma). The adult tissue samples were sonicated three times 10 sec. The protein concentration was determined by Bradford assay (OD 595 nm; Bio-Rad Protein Assay) and 40 μg of each sample were fractionated by SDS-PAGE (Invitrogen; NuPAGE® Novex® 4-12% Bis-Tris Gel). The fractionated extracts were then transferred to a PVDF membrane (iBlot® Dry Blotting System). Membranes were blocked in Tris-buffered saline, 0.2% Tween-20 (TBST) containing 5% or 10% non-fat dry milk, and subsequently incubated with the appropriate primary antibody. Membranes were washed five times with TBST and incubated with either horseradish peroxidase-conjugated horse anti-mouse or goat anti-rabbit secondary antibody (Cell Signaling). After five washes with TBST, proteins were detected by enhanced chemiluminescense "ECL Western Blotting Detection Reagents" (Amersham Biosciences) or "SuperSignal West Femto Maximum Sensitivity Substrate" (Thermo Scientific) and visualized by exposure to X-ray film (Amersham Biosciences). The following primary antibodies were used: rabbit anti-MDM4 (IHC-00108, Bethyl Laboratories), mouse anti-Mdm2 (mixture of 2A10 and 4B2 and SMP14, Santa Cruz Biotechnology), mouse anti-p53 (D0-1, Santa Cruz Biotechnology), mouse anti-p21 (F-5, Santa Cruz Biotechnology), mouse anti-b-Tubulin (Sigma-Aldrich), mouse anti-Vinculin (Sigma-Aldrich).

7. Quantitive Real-Time PCR(RT-qPCR)

RNA was isolated using the "RNeasy minikit" (Qiagen) according to the manufacturer's protocol. The RNA was quantified using a Nanodrop 1000 (Thernioscientific). Two μg of total RNA of each sample of interest was reverse-transcribed using the "High-Capacity cDNA Reverse Transcription Kit" (Applied Biosystems) to obtain cDNA that was further used as template for PCR amplification. Quantitative reverse transcriptase PCR (RT-qPCR) assays were performed using Fast SYBR Green 2× Master Mix, following the manufacturer's instructions (Applied Biosystems). For normalization the geometric mean of at least three reference genes was used. For mouse samples TaqMan probes were designed by Applied Biosystems (assays on demand). For human samples the primers used were as follows: APAF-1 [Fwd, 5'-CCTGT-TGTCTCTTCTTCCAGTGT-3' (SEQ ID NO:1), Rev, 5'-AAAACAACTGGCCTCTGTGG-3' (SEQ ID NO:2)], BAX [Fwd, 5'-ATGTTTTCTGACGGCAACTTC-3' (SEQ ID NO:3), Rev, 5'-ATCAGTTCCGGCACCTTG-3' (SEQ ID NO:4)], MDM4 [Fwd, 5'-AGGTGCGCAAGGTGAAATGT-3' (SEQ ID NO:5), Rev, 5'-CCATATGCTGCTCCTGCT-GAT-3' (SEQ ID NO:6)], MDM2 [Fwd, 5'-AG-GAGATTTGTTTGGCGTGC-3' (SEQ ID NO:7), Rev, 5'-TGAGTCCGATGATTCCTGCTG-3' (SEQ ID NO:8)], PUMA [Fwd, 5'-GACCTCAACGCACAGTA-3' (SEQ ID NO:9), Rev, 5'-CTAATTGGGCTCCATCT-3' (SEQ ID NO:10)], p21 [Fwd, 5'-AGCAGAGGAAGACCATGTGGA-3' (SEQ ID NO:11), Rev, 5'-AATCTGTCATGCTGGTCT-GCC-3' (SEQ ID NO:12)]. The following reference genes were used: GAPDH [Fwd, 5'-TGCCATGTAGACCCCT-TGAAG-3' (SEQ ID NO:13), Rev, 5'-ATGGTACATGA-CAAGGTGCGG-3' (SEQ ID NO:14)], HMBS [Fwd, 5'-GGCAATGCGGCCTGCAA-3' (SEQ ID NO:15), Rev, 5'-GGGTACCCACGCGAATCAC-3' (SEQ ID NO:16)], RLP13a [Fwd, 5'-CCTGGAGGAGAAGAGGAAAGAGA-3' (SEQ ID NO:17), Rev, 5'-TTGAGGACCTCTGTG-TATTTGTCAA-3' (SEQ ID NO:18)], TBP [Fwd, 5'-CG-GCTGTTTAACTTCGCTTC-3' (SEQ ID NO:19), Rev, 5'-CACACGCCAAGAAACAGTGA-3' (SEQ ID NO:20)]. Gene expression levels and errors on the gene expression levels were calculated using qBasePLUS 1.0 analysis software.[59]

8. Determining the BRAF and NRAS Status

To analyze the mutational status of BRAF and NRAS in the short-term melanoma cell lines, 200 ng of cDNA from each of the cell line was used as a template for a PCR reaction. The subsequent primer sequences were used for genotyping: Primer BRAF [Fwd, 5'-AGCACCTACACCTCAGCAGT-TACA-3' (SEQ ID NO:21), Rev, 5'-ACAGGTATCCTCGTC-CCACCATAA-3' (SEQ ID NO:22)], Primer NRAS [Fwd, 5'-ACAAACTGGTGGTGGTTGGA-3' (SEQ ID NO:23), Rev, 5'-TGGCCATCCCATACAACCCT-3' (SEQ ID NO:24)].

Subsequently, PCR reaction was purified using the QIAquick PCR Purification Kit, according to the manufacturer's protocol. The purified PCR products were sequenced using following nested primers: Primer BRAF (Nested) 5'-AGGGCATGGATTACTTACACGCCA-3' (SEQ ID NO:25), Primer NRAS (Nested) 5'-ACTCGCTTAATCT-GCTCCCTGT-3' (SEQ ID NO:26).

9. Histology and IHC

Tissues were fixed overnight in 4% paraformaldehyde, dehydrated, paraffin embedded, sectioned (6 um) and stained with hematoxylin and eosin (H&E). For immunohistochemistry (IHC), slides were bleached for 5 hours in 10% $H_2O_2$ solution, and stained with antibodies against S100 (rabbit, Z0311, 1:300; Dako). Detection was performed with the secondary goat anti-rabbit antibody (E0432, 1:500; Dako) combined with the incubation in an ABC reagent (Vector). Sections were counterstained with hematoxylin.

10. Xenograft Experiments

All animal experiments were performed in accordance with the guidelines of the University of Leuven Animal Care and Use ethical Committee. Mice were injected subcutaneously with human cell lines in sterile phosphate buffered saline [PBS 1× (pH 7.4)]. MM031 xenografts were established by injecting $10^7$ cells, whereas Lu1205 and A375 xenografts were established by injecting $10^6$ cells subcutaneously into the flanks of eight-week-old female Rj:NMRI-nu (nu/nu) mice (Jackson Labs). For the knock-down experiments, tumor growth was monitored with a caliper twice a week, and the volume was calculated using the following formula $V=a*b^2*0.5$, where a is the largest, and b the smallest diameter of the tumor. The SAH-p53-8 experiment was performed on MM031 cell line-derived tumors with an average volume of 200 $mm^3$. Subsequently, cohorts (n=7) were treated with vehicle (5% DMSO in D5W) or SAH-p53-8 (10 mg/kg), once daily for five consecutive days by intravenous injection and tumor volume was monitored by caliper measurement daily for a period of 12 days.

REFERENCES

1. Chin, L., Garraway, L. A. & Fisher, D. E. Malignant melanoma: genetics and therapeutics in the genomic era. *Genes Dev.* 20, 2149-2182 (2006).
2. Ibrahim, N. & Haluska, F. G. Molecular pathogenesis of cutaneous melanocytic neoplasms. *Annual review of pathology* 4, 551-579 (2009).
3. Davies, M. A. & Samuels, Y. Analysis of the genome to personalize therapy for melanoma. *Oncogene* 29, 5545-5555.
4. Cohen, C., et al. Mitogen-actived protein kinase activation is an early event in melanoma progression. *Clin. Cancer Res.* 8, 3728-3733 (2002).
5. Demunter, A., Stas, M., Degreef, H., De Wolf-Peeters, C. & van den Oord, J. J. Analysis of N- and K-ras mutations in the distinctive tumor progression phases of melanoma. *J. Invest. Dermatol.* 117, 1483-1489 (2001).
6. Papp, T., et al. Mutational analysis of the N-ras, p53, p16INK4a, CDK4, and MC1R genes in human congenital melanocytic naevi. *J. Med. Genet.* 36, 610-614 (1999).
7. Davies, H., et al. Mutations of the BRAF gene in human cancer. *Nature* 417, 949-954 (2002).
8. Gray-Schopfer, V. C., da Rocha Dias, S. & Marais, R. The role of B-RAF in melanoma. *Cancer metastasis reviews* 24, 165-183 (2005).
9. Nazarian, R., et al. Melanomas acquire resistance to B-RAF(V600E) inhibition by RTK or N-RAS up-regulation. *Nature* 468, 973-977 (2010).
10. Lane, D. P., Cheok, C. F. & Lain, S. p53-based cancer therapy. *Cold Spring Harb Perspect. Biol.* 2, a001222.
11. Brown, C. J., Lain, S., Verma, C. S., Fersht, A. R. & Lane, D. P. Awakening guardian angels: drugging the p53 pathway. *Nat. Rev. Cancer* 9, 862-873 (2009).
12. Wade, M. & Wahl, G. M. Targeting Mdm2 and Mdmx in cancer therapy: better living through medicinal chemistry? *Mol. Cancer. Res.* 7, 1-11 (2009).
13. Vousden, K. H. & Prives, C. Blinded by the Light: The Growing Complexity of p53. *Cell* 137, 413-431 (2009).
14. Chin, L. The genetics of malignant melanoma: lessons from mouse and man. *Nat. Rev. Cancer* 3, 559-570 (2003).
15. Bardeesy, N., et al. Dual inactivation of RB and p53 pathways in RAS-induced melanomas. *Mol. Cell. Biol.* 21, 2144-2153 (2001).
16. Goel, V. K., et al. Melanocytic nevus-like hyperplasia and melanoma in transgenic BRAFV600E mice. *Oncogene* 28, 2289-2298 (2009).
17. Dovey, M., White, R. M. & Zon, L. I. Oncogenic NRAS cooperates with p53 loss to generate melanoma in zebrafish. *Zebrafish* 6, 397-404 (2009).
18. Vogelstein, B., Lane, D. & Levine, A. J. Surfing the p53 network. *Nature* 408, 307-310 (2000).
19. Marine, J. C. & Lozano, G. Mdm2-mediated ubiquitylation: p53 and beyond. *Cell death and differentiation* 17, 93-102 (2010).
20. Muthusamy, V., et al. Amplification of CDK4 and MDM2 in malignant melanoma. *Genes Chromosomes Cancer* 45, 447-454 (2006).
21. Hocker, T. & Tsao, H. Ultraviolet radiation and melanoma: a systematic review and analysis of reported sequence variants. *Hum. Mutat.* 28, 578-588 (2007).
22. Sherr, C. J. The INK4a/ARF network in tumour suppression. *Nat. Rev. Mol. Cell. Biol.* 2, 731-737 (2001).
23. Ha, L., et al. ARF functions as a melanoma tumor suppressor by inducing p53-independent senescence. *Proc. Natl. Acad. Sci. U.S.A.* 104, 10968-10973 (2007).
24. Marine, J. C. & Jochemsen, A. G. Mdmx as an essential regulator of p53 activity. *Biochem. Biophys. Res. Commun.* 331, 750-760 (2005).
25. Toledo, F. & Wahl, G. M. Regulating the p53 pathway: in vitro hypotheses, in vivo veritas. *Nat. Rev. Cancer* 6, 909-923 (2006).
26. Houben, R., et al. High-level expression of wild-type p53 in melanoma cells is frequently associated with inactivity in p53 reporter gene assays. *PloS one* 6, e22096 (2011).
27. Danovi, D., et al. Amplification of Mdmx (or Mdm4) directly contributes to tumor formation by inhibiting p53 tumor suppressor activity. *Mol. Cell. Biol.* 24, 5835-5843 (2004).
28. Laurie, N. A., et al. Inactivation of the p53 pathway in retinoblastoma. *Nature* 444, 61-66 (2006).
29. Beroukhim, R., et al. The landscape of somatic copy-number alteration across human cancers. *Nature* 463, 899-905 (2010).
30. Kabbarah, O., et al. Integrative genome comparison of primary and metastatic melanomas. *PLoS One* 5, e10770 (2010).
31. Vassilev, L. T., et al. In vivo activation of the p53 pathway by small-molecule antagonists of MDM2. *Science* 303, 844-848 (2004).
32. el-Deiry, W. S., et al. WAF1, a potential mediator of p53 tumor suppression. *Cell* 75, 817-825 (1993).
33. Ackermann, J., et al. Metastasizing melanoma formation caused by expression of activated N-RasQ61K on an INK4a-deficient background. *Cancer Res.* 65, 4005-4011 (2005).
34. Ohsie, S. J., Sarantopoulos, G. P., Cochran, A. J. & Binder, S. W. Immunohistochemical characteristics of melanoma. *J. Cutan. Pathol.* 35, 433-444 (2008).

35. Ferguson, B., et al. Differential roles of the pRb and Arf/p53 pathways in murine naevus and melanoma genesis. *Pigment cell & melanoma research* 23, 771-780 (2010).
36. De Clercq, S., et al. Widespread overexpression of epitope-tagged Mdm4 does not accelerate tumor formation in vivo. *Mol. Cell. Biol.* 30, 5394-5405 (2010).
37. Jacks, T., et al. Tumor spectrum analysis in p53-mutant mice. *Curr. Biol.* 4, 1-7 (1994).
38. Marine, J. C., Dyer, M. A. & Jochemsen, A. G. MDMX: from bench to bedside. *J. Cell Sci.* 120, 371-378 (2007).
39. Bernal, F., Tyler, A. F., Korsmeyer, S. J., Walensky, L. D. & Verdine, G. L. Reactivation of the p53 tumor suppressor pathway by a stapled p53 peptide. *J. Am. Chem. Soc.* 129, 2456-2457 (2007).
40. Bernal, F., et al. A stapled p53 helix overcomes HDMX-mediated suppression of p53. *Cancer Cell* 18, 411-422 (2010).
41. Chapman, P. B., et al. Phase III multicenter randomized trial of the Dartmouth regimen versus dacarbazine in patients with metastatic melanoma. *J. Clin. Oncol.* 17, 2745-2751 (1999).
42. Fedorenko, I. V., Paraiso, K. H. & Smalley, K. S. Acquired and intrinsic BRAF inhibitor resistance in BRAF V600E mutant melanoma. *Biochemical pharmacology* 82, 201-209 (2011).
43. Villanueva, J., et al. Acquired resistance to BRAF inhibitors mediated by a RAF kinase switch in melanoma can be overcome by cotargeting MEK and IGF-1R/PI3K. *Cancer cell* 18, 683-695 (2010).
44. Garcia, D., et al. Validation of MdmX as a therapeutic target for reactivating p53 in tumors. *Genes & development* 25, 1746-1757 (2011).
45. Martins, C. P., Brown-Swigart, L. & Evan, G. I. Modeling the therapeutic efficacy of p53 restoration in tumors. *Cell* 127, 1323-1334 (2006).
46. Ventura, A., et al. Restoration of p53 function leads to tumour regression in vivo. *Nature* 445, 661-665 (2007).
47. Xue, W., et al. Senescence and tumour clearance is triggered by p53 restoration in murine liver carcinomas. *Nature* 445, 656-660 (2007).
48. Canner, J. A., et al. MI-63: a novel small-molecule inhibitor targets MDM2 and induces apoptosis in embryonal and alveolar rhabdomyosarcoma cells with wild-type p53. *British journal of cancer* 101, 774-781 (2009).
49. Hedstrom, E., Issaeva, N., Enge, M. & Selivanova, G. Tumor-specific induction of apoptosis by a p53-reactivating compound. *Experimental cell research* 315, 451-461 (2009).
50. Issaeva, N., et al. Small molecule RITA binds to p53, blocks p53-HDM-2 interaction and activates p53 function in tumors. *Nature medicine* 10, 1321-1328 (2004).
51. Shangary, S., et al. Reactivation of p53 by a specific MDM2 antagonist (MI-43) leads to p21-mediated cell cycle arrest and selective cell death in colon cancer. *Molecular cancer therapeutics* 7, 1533-1542 (2008).
52. Marine, J. C. MDM2 and MDMX in cancer and development. *Current topics in developmental biology* 94, 45-75 (2011).
53. Flaherty, K. T. Chemotherapy and targeted therapy combinations in advanced melanoma. *Clin. Cancer Res.* 12, 2366s-2370s (2006).
54. Flaherty, K. T., et al. Inhibition of mutated, activated BRAF in metastatic melanoma. *The New England journal of medicine* 363, 809-819 (2010).
55. Lam, S., et al. Role of Mdm4 in drug sensitivity of breast cancer cells. *Oncogene* 29, 2415-2426 (2010).
56. Brummelkamp, T. R., Bernards, R. & Agami, R. A system for stable expression of short interfering RNAs in mammalian cells. *Science* 296, 550-553 (2002).
57. van de Wetering, M., et al. Specific inhibition of gene expression using a stably integrated, inducible small-interfering-RNA vector. *EMBO Rep.* 4, 609-615 (2003).
58. Carlotti, F., et al. Lentiviral vectors efficiently transduce quiescent mature 3T3-L1 adipocytes. *Mol. Ther.* 9, 209-217 (2004).
59. Vandesompele, J., et al. Accurate normalization of real-time quantitative RT-PCR data by geometric averaging of multiple internal control genes. *Genome Biol.* 3, RESEARCH0034 (2002).
60. Migliorini, D., et al. Mdm4 (Mdmx) regulates p53-induced growth arrest and neuronal cell death during early embryonic mouse development. *Mol. Cell. Biol.* 22, 5527-5538 (2002).

What is claimed is:

1. A pharmaceutical composition useful for treating a subject suffering from melanoma resistant to a Raf kinase inhibitor, the pharmaceutical composition comprising:
   i) an amount of a stapled peptide effective to inhibit interaction between MDM4 and p53; and
   ii) an effective amount of a Raf kinase inhibitor;
   wherein when the pharmaceutical composition is administered to the subject suffering from melanoma, the components of the pharmaceutical composition act synergistically to increase the cytotoxicity of the pharmaceutical composition to melanoma cells resistant to a Raf kinase inhibitor in the subject.

2. The pharmaceutical composition of claim 1, wherein the Raf kinase inhibitor comprises a B-raf kinase inhibitor.

3. A method for treating a patient having melanoma, the method comprising:
   determining the protein expression level of MDM4 in a melanoma tumor sample derived from the patient and,
   when an enhanced MDM4 protein expression compared to the MDM2 protein expression selects the patient for administering a therapeutically effective amount of a pharmaceutical composition, administering the pharmaceutical composition according to claim 1 to the patient.

4. A method for treating a patient having melanoma, the method comprising:
   determining the protein expression level of MDM4 and the B-RAF status in a melanoma tumor sample derived from the patient and,
   when an enhanced MDM4 protein expression compared to the MDM2 protein expression and the presence of a B-RAF mutation selects the patient for administering a therapeutically effective amount of a pharmaceutical composition according to claim 1, administering the pharmaceutical composition to the patient.

5. The composition of claim 1, wherein the stapled peptide is SAH-p53-8.

6. The composition of claim 1, wherein the Raf kinase inhibitor is PLX4032.

7. The composition of claim 1, wherein the stapled peptide is SAH-p53-8 and the Raf kinase inhibitor is PLX4032.

8. A method for treating a subject suffering from melanoma, the method comprising: administering the pharmaceutical composition of claim 1 to the subject for simultaneous, concurrent, separate or sequential use in for treating melanoma.

9. The method according to claim 8, wherein said melanoma is advanced cutaneous melanoma.

10. The method according to claim 8, wherein said melanoma has an activating B-RAF mutation.

11. The method according to claim 10, wherein said melanoma having an activating B-RAF mutation has acquired a resistance to a B-RAF inhibitor.

12. The method according to claim 10, wherein said melanoma has additionally an enhanced protein expression level of MDM4.

* * * * *

SEQUENCE LISTING

<160> NUMBER OF SEQ ID NOS: 26

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
cctgttgtct cttcttccag tgt                                    23

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
aaaacaactg gcctctgtgg                                        20

```
<210> SEQ ID NO 3
<211> LENGTH: 21
<212> TYPE: DNA
<213> ORGANISM: Artificial Sequence
<220> FEATURE:
<223> OTHER INFORMATION: Primer

<400> SEQUENCE: 3
atgttttctg acggcaactt c                                              21

<210> SEQ ID NO 4
<211> LENGTH: 18
<212> TYPE: DNA
<213> ORGANISM: Artificial Sequence
<220> FEATURE:
<223> OTHER INFORMATION: Primer

<400> SEQUENCE: 4
atcagttccg gcaccttg                                                  18

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
aggtgcgcaa ggtgaaatgt                                                20

<210> SEQ ID NO 6
<211> LENGTH: 21
<212> TYPE: DNA
<213> ORGANISM: Artificial Sequence
<220> FEATURE:
<223> OTHER INFORMATION: Primer

<400> SEQUENCE: 6
ccatatgctg ctcctgctga t                                              21

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
aggagatttg tttggcgtgc                                                20

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
tgagtccgat gattcctgct g                                              21

<210> SEQ ID NO 9
<211> LENGTH: 17
<212> TYPE: DNA
<213> ORGANISM: Artificial Sequence
<220> FEATURE:
<223> OTHER INFORMATION: Primer
```

<400> SEQUENCE: 9
gacctcaacg cacagta                                                          17

<210> SEQ ID NO 10
<211> LENGTH: 17
<212> TYPE: DNA
<213> ORGANISM: Artificial Sequence
<220> FEATURE:
<223> OTHER INFORMATION: Primer

<400> SEQUENCE: 10
ctaattgggc tccatct                                                          17

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
agcagaggaa gaccatgtgg a                                                     21

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
aatctgtcat gctggtctgc c                                                     21

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
tgccatgtag accccttgaa g                                                     21

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
atggtacatg acaaggtgcg g                                                     21

<210> SEQ ID NO 15
<211> LENGTH: 16
<212> TYPE: DNA
<213> ORGANISM: Artificial Sequence
<220> FEATURE:
<223> OTHER INFORMATION: Primer

<400> SEQUENCE: 15
ggcaatgcgg ctgcaa                                                           16

```
<210> SEQ ID NO 16
<211> LENGTH: 19
<212> TYPE: DNA
<213> ORGANISM: Artificial Sequence
<220> FEATURE:
<223> OTHER INFORMATION: Primer

<400> SEQUENCE: 16
gggtacccac gcgaatcac                                               19

<210> SEQ ID NO 17
<211> LENGTH: 23
<212> TYPE: DNA
<213> ORGANISM: Artificial Sequence
<220> FEATURE:
<223> OTHER INFORMATION: Primer

<400> SEQUENCE: 17
cctggaggag aagaggaaag aga                                          23

<210> SEQ ID NO 18
<211> LENGTH: 25
<212> TYPE: DNA
<213> ORGANISM: Artificial Sequence
<220> FEATURE:
<223> OTHER INFORMATION: Primer

<400> SEQUENCE: 18
ttgaggacct ctgtgtattt gtcaa                                        25

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
cggctgttta acttcgcttc                                              20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
cacacgccaa gaaacagtga                                              20

<210> SEQ ID NO 21
<211> LENGTH: 24
<212> TYPE: DNA
<213> ORGANISM: Artificial Sequence
<220> FEATURE:
<223> OTHER INFORMATION: Primer

<400> SEQUENCE: 21
agcacctaca cctcagcagt taca                                         24

<210> SEQ ID NO 22
<211> LENGTH: 24
<212> TYPE: DNA
<213> ORGANISM: Artificial Sequence
<220> FEATURE:
<223> OTHER INFORMATION: Primer
```

```
<400> SEQUENCE: 22
acaggtatcc tcgtcccacc ataa                                          24

<210> SEQ ID NO 23
<211> LENGTH: 20
<212> TYPE: DNA
<213> ORGANISM: Artificial Sequence
<220> FEATURE:
<223> OTHER INFORMATION: Primer

<400> SEQUENCE: 23
acaaactggt ggtggttgga                                               20

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
tggccatccc atacaaccct                                               20

<210> SEQ ID NO 25
<211> LENGTH: 24
<212> TYPE: DNA
<213> ORGANISM: Artificial Sequence
<220> FEATURE:
<223> OTHER INFORMATION: Primer

<400> SEQUENCE: 25
agggcatgga ttacttacac gcca                                          24

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
actcgcttaa tctgctccct gt                                            22
```